United States Patent
Badenoch et al.

(10) Patent No.: US 11,559,488 B2
(45) Date of Patent: Jan. 24, 2023

(54) PHARMACEUTICAL COMPOSITIONS HAVING HIGH DRUG LOADINGS OF MEDIUM CHAIN TRIGLYCERIDES AND METHODS RELATED THERETO

(71) Applicant: Cerecin Inc., Denver, CO (US)

(72) Inventors: Aaron M. Badenoch, Bend, OR (US); Taryn Boivin, Surry (CA); Devon B. DuBose, Bend, OR (US); Samuel T. Henderson, Golden, CO (US); Christi Lynn Hostetler, Bend, OR (US); David K. Lyon, Bend, OR (US); Craig A. Sather, Bend, OR (US); Matthew J. Shaffer, Bend, OR (US)

(73) Assignee: Cerecin Inc., Denver, CO (US)

( * ) Notice: Subject to any disclaimer, the term of this patent is extended or adjusted under 35 U.S.C. 154(b) by 77 days.

(21) Appl. No.: 16/493,963

(22) PCT Filed: Mar. 15, 2018

(86) PCT No.: PCT/US2018/022594
§ 371 (c)(1),
(2) Date: Sep. 13, 2019

(87) PCT Pub. No.: WO2018/170235
PCT Pub. Date: Sep. 20, 2018

(65) Prior Publication Data
US 2021/0220277 A1    Jul. 22, 2021

Related U.S. Application Data

(60) Provisional application No. 62/471,836, filed on Mar. 15, 2017.

(51) Int. Cl.
| | |
|---|---|
| *A61K 31/23* | (2006.01) |
| *A61K 9/16* | (2006.01) |
| *A61K 9/107* | (2006.01) |
| *A61P 25/28* | (2006.01) |
| *B82Y 5/00* | (2011.01) |
| *B82Y 30/00* | (2011.01) |
| *B82Y 40/00* | (2011.01) |

(52) U.S. Cl.
CPC .......... *A61K 9/1617* (2013.01); *A61K 9/1075* (2013.01); *A61K 9/1611* (2013.01); *A61K 9/1635* (2013.01); *A61K 9/1682* (2013.01); *A61K 31/23* (2013.01); *B82Y 5/00* (2013.01); *B82Y 30/00* (2013.01); *B82Y 40/00* (2013.01)

(58) Field of Classification Search
CPC .. A61K 9/1617; A61K 9/1075; A61K 9/1611; A61K 9/1635; A61K 9/1682; A61K 31/23; A23K 20/158; A23L 33/15; A23L 33/12; A61P 25/28
See application file for complete search history.

(56) References Cited

U.S. PATENT DOCUMENTS

| | | | |
|---|---|---|---|
| 5,422,363 A | 6/1995 | Yanai et al. | |
| 6,169,087 B1 | 1/2001 | Bunnell et al. | |
| 6,923,988 B2 * | 8/2005 | Patel ................... | A61K 9/4858 424/489 |
| 8,445,535 B1 | 5/2013 | Henderson | |
| 9,415,012 B2 | 8/2016 | Richard et al. | |
| 2003/0180235 A1 | 9/2003 | Grisoni et al. | |
| 2007/0292461 A1 * | 12/2007 | Tamarkin ............... | A61P 31/12 424/401 |
| 2008/0009467 A1 | 1/2008 | Henderson | |
| 2008/0181962 A1 * | 7/2008 | Brzeczko ................ | C08J 3/122 424/489 |
| 2010/0239685 A1 | 9/2010 | Kwak et al. | |
| 2011/0165140 A1 | 7/2011 | Brader et al. | |
| 2011/0312973 A1 | 12/2011 | Liepold et al. | |
| 2012/0196932 A1 | 8/2012 | Henderson | |
| 2013/0225682 A1 | 8/2013 | Henderson | |
| 2014/0271845 A1 * | 9/2014 | Shah .................... | A61K 31/454 424/463 |
| 2016/0095827 A1 * | 4/2016 | Powell ................. | A61K 9/4808 424/458 |
| 2016/0354335 A1 | 12/2016 | Cohen et al. | |
| 2017/0296501 A1 | 10/2017 | Lowery et al. | |
| 2018/0036274 A1 | 2/2018 | Henderson | |

FOREIGN PATENT DOCUMENTS

| | | |
|---|---|---|
| CA | 2632550 | 6/2007 |
| CN | 101919453 | 12/2010 |
| CN | 104054849 | 9/2014 |
| CN | 105395492 | 3/2016 |
| EP | 2319508 | 5/2011 |

(Continued)

OTHER PUBLICATIONS

Pouton, Formulation of poorly water-soluble drugs for oral administration: Physicochemical and physiological issues and the lipid formulation classification system, European Journal of Pharmaceutical Sciences, 29(3-4), pp. 278-287. (Year: 2006).*

(Continued)

*Primary Examiner* — Abigail Vanhorn
(74) *Attorney, Agent, or Firm* — Polsinelli PC

(57) ABSTRACT

This invention relates to high drug load compositions of medium chain triglycerides (MCT), and to methods for treatment with such compositions at amounts effective to elevate ketone body concentrations so as to treat conditions associated with reduced neuronal metabolism, for example Alzheimer's disease.

25 Claims, 19 Drawing Sheets

(56) References Cited

FOREIGN PATENT DOCUMENTS

| WO | WO 94/08610 | 4/1994 |
| WO | WO 00/67728 | 11/2000 |
| WO | WO 2014/132134 | 9/2014 |
| WO | WO 2016/210180 | 12/2016 |
| WO | WO 2017/149392 | 9/2017 |
| WO | WO 2019/178482 | 9/2019 |
| WO | WO 2020/011747 | 1/2020 |
| WO | WO 2020/180980 | 9/2020 |

OTHER PUBLICATIONS

Vehring R. Pharmaceutical particle engineering via spray drying. Pharm Res. 2008;25(5):999-1022. (Year: 2008).*

Hasselbalch, S.G., et al., Changes in cerebral blood flow and carbohydrate metabolism during acute hyperketonemia, *Am J Physiol*, 1996, 270:E746-51.

Veneman, T., et al., Effect of hyperketonemia and hyperlacticacidemia on symptoms, cognitive dysfunction, and counterregulatory hormone responses during hypoglycemia in normal humans, *Diabetes*, 1994, 43:1311-7.

Hansen et al., "Process characteristics and compaction of spray-dried emulsions containing a drug dissolved in lipid," *International Journal of Pharmaceutics* 287 (2004) 55-66.

Henderson et al., "Pharmocogenetic analysis of the effects of polymorphisms in APOE, IDE and IL1B on a ketone body based therapeutic on cognition in mild to moderate Alzheimer's disease; a randomized, double-blind, placebo-controlled study," *BMC Medical Genetics* 2011, 12:137, 14 pages.

Schaffazick et al., "Development of Nanocapsule Suspensions and Nanocapsule Spray-Dried Powders Containing Melatonin," *J. Braz. Chem. Soc.*, vol. 17, No. 3, 562-569, 2006.

Shao et al., "Development and evaluation of self-microemulsifying liquid and granule formulations of *Brucea javanica* oil," *Arch. Pharm. Res.* (2013) 36:993-1003.

Accera, Axona Description, Nov. 2012, retrieved from http://www.about-axona.com/assets/files/us-en/global/pdf/Asona-PrescribingInformation.pdf.

Cunnane et al., "Can ketones compensate for deteriorating brain glucose uptake during aging? Implications for the risk and treatment of Alzheimer's Disease," *Ann. N.Y. Acad. Sci.*, 1367 (2016) 12-20.

Vandenberghe et al., "Tricaprylin Alone Increases Plasma Ketone Response More Than Coconut Oil or Other Medium-Chain Triglycerides: An Acute Crossover Study in Health Adults," Current Developments in Nutrition, Mar. 22, 2017, 5 pages.

Walker et al., "Development of tricaprilin, a ketogenicdrug for Alzheimer's disease," Jul. 2020, AAIC Jul. 26-30, 2020, Poster #38787.

Uges, Plasma or serum in therapeutic drug monitoring and clinical toxicology, Pharmaceutisch Weekblad Scientific Edition 1988, vol. 10, pp. 185-188.

Reger et al., "Effects of β-hydroxybutyrate on cognition in memory-impaired adults," *Neurobiology of Aging* 25 (2004) 311-314.

Henderson et al., "Study of the ketogenic agent AC-1202 in mild to moderate Alzheimer's disease: a randomized, double-blind, placebo-controlled, multicenter trial," *Nutrition and Metabolism 2009*, 6:31.

Courchesne-Loyer et al., "Emulsification Increases the Acute Ketogenic Effect and Bioavailability of Medium-Chain Triglycerides in Humans," *Curr Dev Nutr* 2017; 8 pages.

Friberg et al., "Phase Equilibria and Their Influence on the Properties of Emulsions," *Journal of the American Oil Chemists' Society*, May 1970, vol. 47, pp. 149-152.

Prajapati et al.," A Comparative Evaluation of Mono-, Di-and Triglyceride of Medium Chain Fatty Acids by Lipid/Surfactant/Water Phase Diagram, Solubility Determination and Dispersion Testing for Application in Pharmaceutical Dosage Form Development," *Pharm Res* (2012) 29:285-305.

Kim et al., "Tricaprylin microemulsion for oral delivery of low molecular weight heparin conjugates," *Journal of Controlled Release* 105 (2005) 32-42.

* cited by examiner

100

| PREPARATION OF LIPID MIXTURE |
|---|
| Add lipid and surfactant mixture to lipid mixture preparation vessel<br><br>Add MCT and Surfactants<br>Add any Co-Surfactant<br><br>102 |

| SOLVENT ADDITION |
|---|
| Add solvent to solution preparation vessel<br><br>Solvent<br><br>104 |

| OPTIONAL FILM FORMING POLYMER ADDITION |
|---|
| Add optional film forming polymer to solution preparation vessel<br><br>Optional Film Forming Polymer<br><br>106 |

| ADSORBENT ADDITION |
|---|
| Add adsorbent to solution preparation vessel<br><br>Adsorbent<br><br>108 |

| LIPID MIXTURE ADDITION |
|---|
| Add Lipid Mixture to solution preparation vessel to form final solution preparation<br><br>Lipid Mixture<br><br>110 |

| SPRAY-DRYING |
|---|
| Spray dry final solution preparation in spray drier with desired spray dry parameters<br><br>Spray Dry<br><br>112 |

FIGURE 1

(60% API)

(50% API)

(40% API)

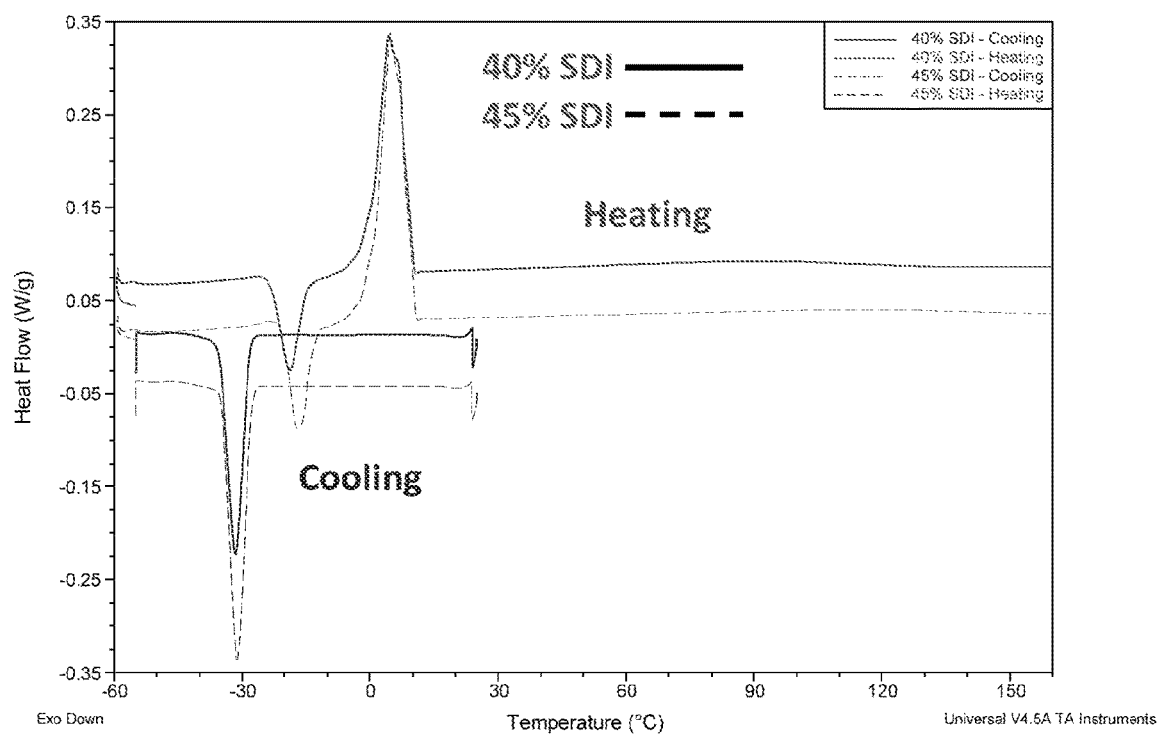
FIGURE 5
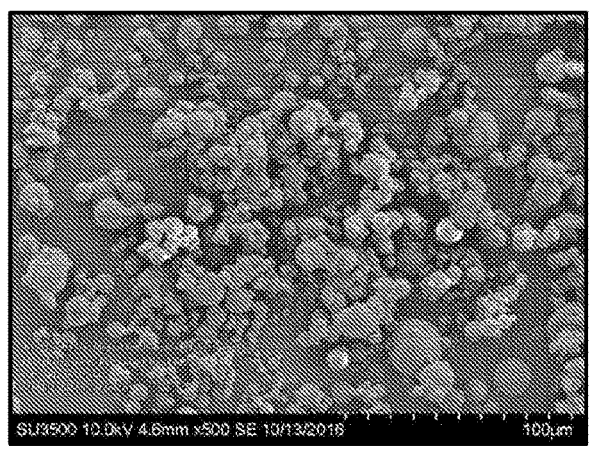 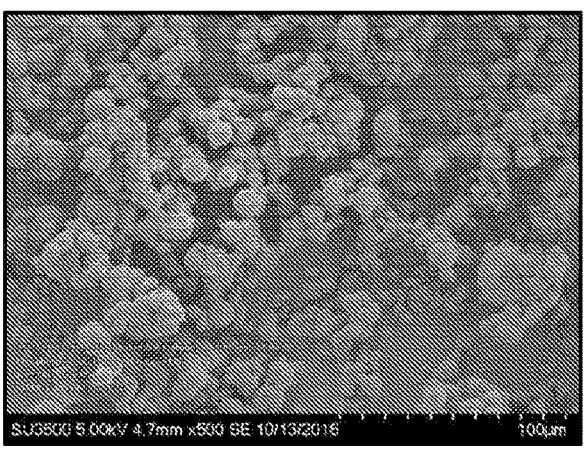
FIGURE 6A                               FIGURE 6B

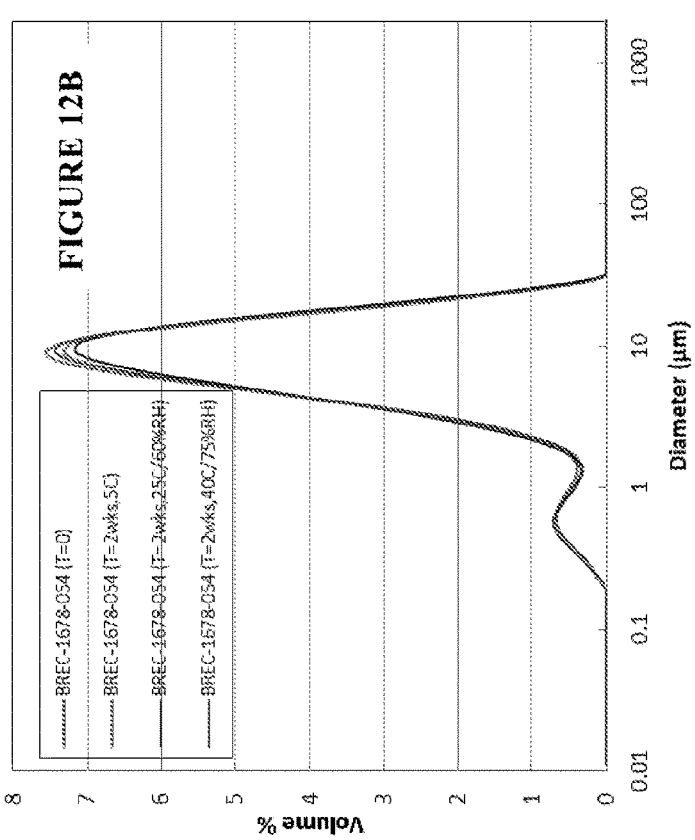
FIGURE 12A
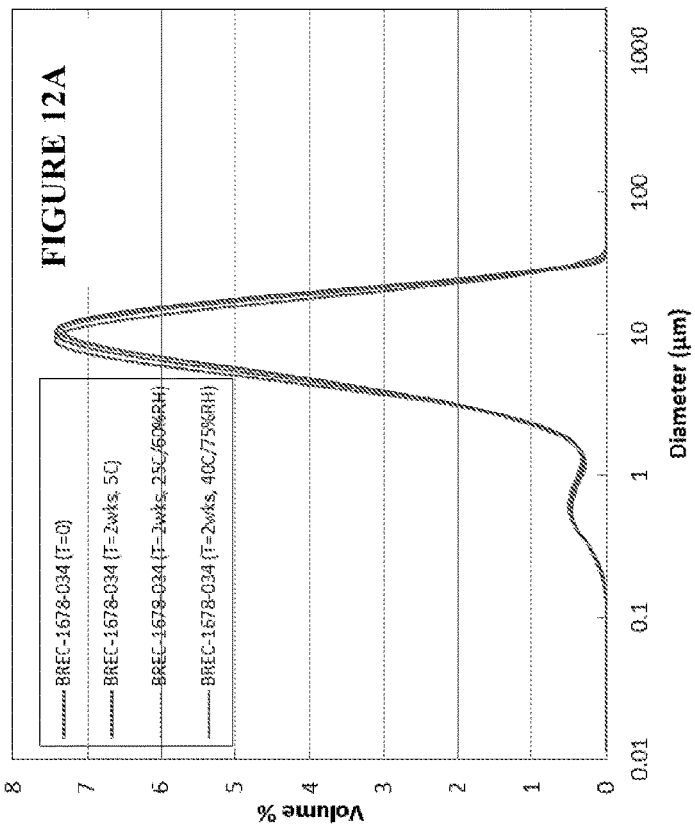
FIGURE 12B
| Test Ref: BREC-1678-098 | | | Averages | | | | | |
|---|---|---|---|---|---|---|---|---|
| % AC-1204 | Storage Condition | Lot | D(v 0.1) μm | D(v 0.5) μm | D(v 0.9) μm | D[3,2] μm | D[4,3] μm | Span |
| 40% AC-1204 | T=0 | BREC-1678-034 | 3 | 8 | 16 | 4 | 9 | 1.759 |
|  | T=2 Weeks, 5°C |  | 3 | 8 | 17 | 4 | 9 | 1.751 |
|  | T=2 Weeks, 25°C/60%RH |  | 3 | 8 | 17 | 4 | 9 | 1.769 |
|  | T=2 Weeks, 40°C/75%RH |  | 3 | 8 | 17 | 4 | 9 | 1.757 |
| 45% AC-1204 | T=0 | BREC-1678-054 | 2 | 7 | 15 | 3 | 8 | 1.775 |
|  | T=2 Weeks, 5°C |  | 2 | 7 | 16 | 3 | 8 | 1.795 |
|  | T=2 Weeks, 25°C/60%RH |  | 2 | 7 | 16 | 3 | 8 | 1.830 |
|  | T=2 Weeks, 40°C/75%RH |  | 2 | 7 | 16 | 3 | 8 | 1.778 |
FIGURE 12C

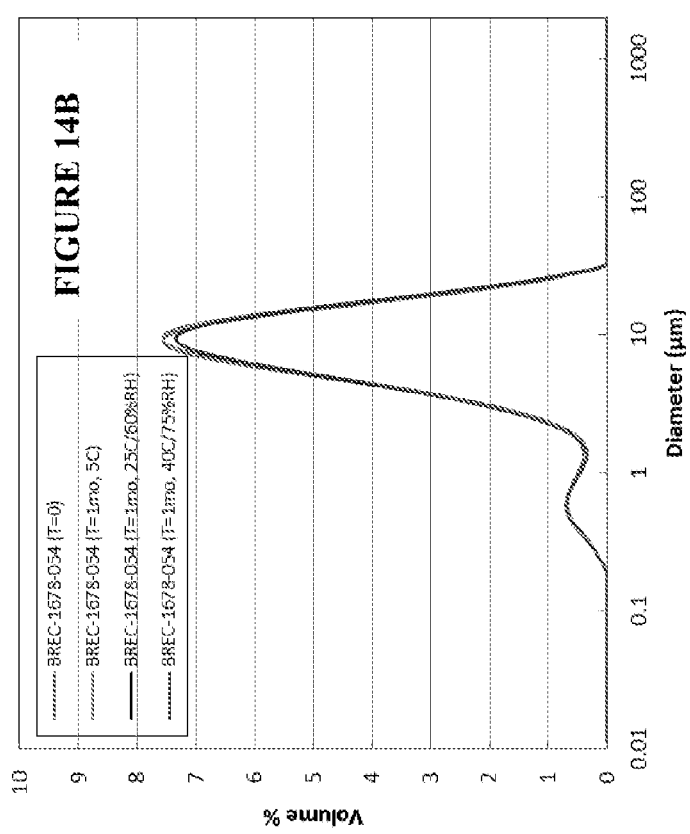
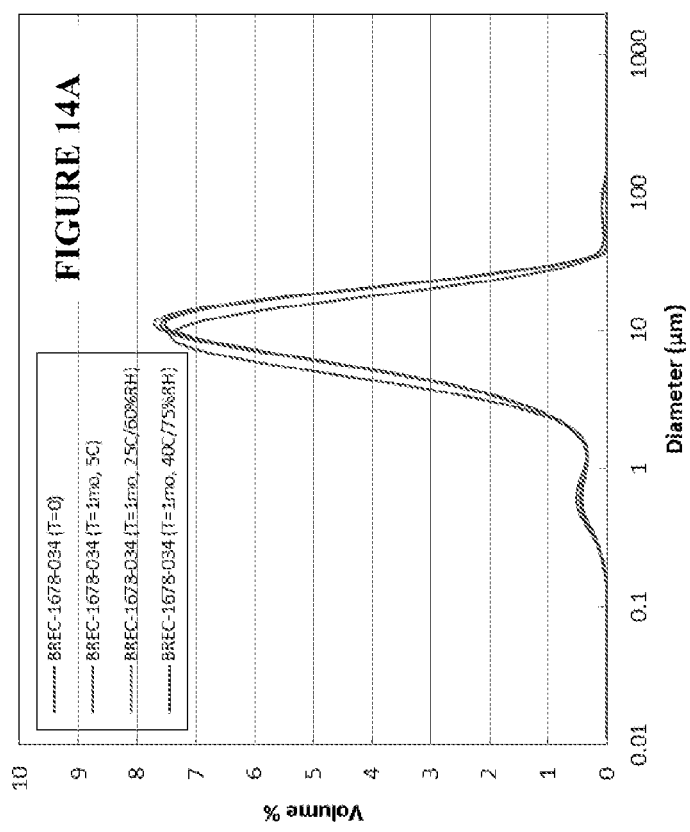
FIGURE 14C

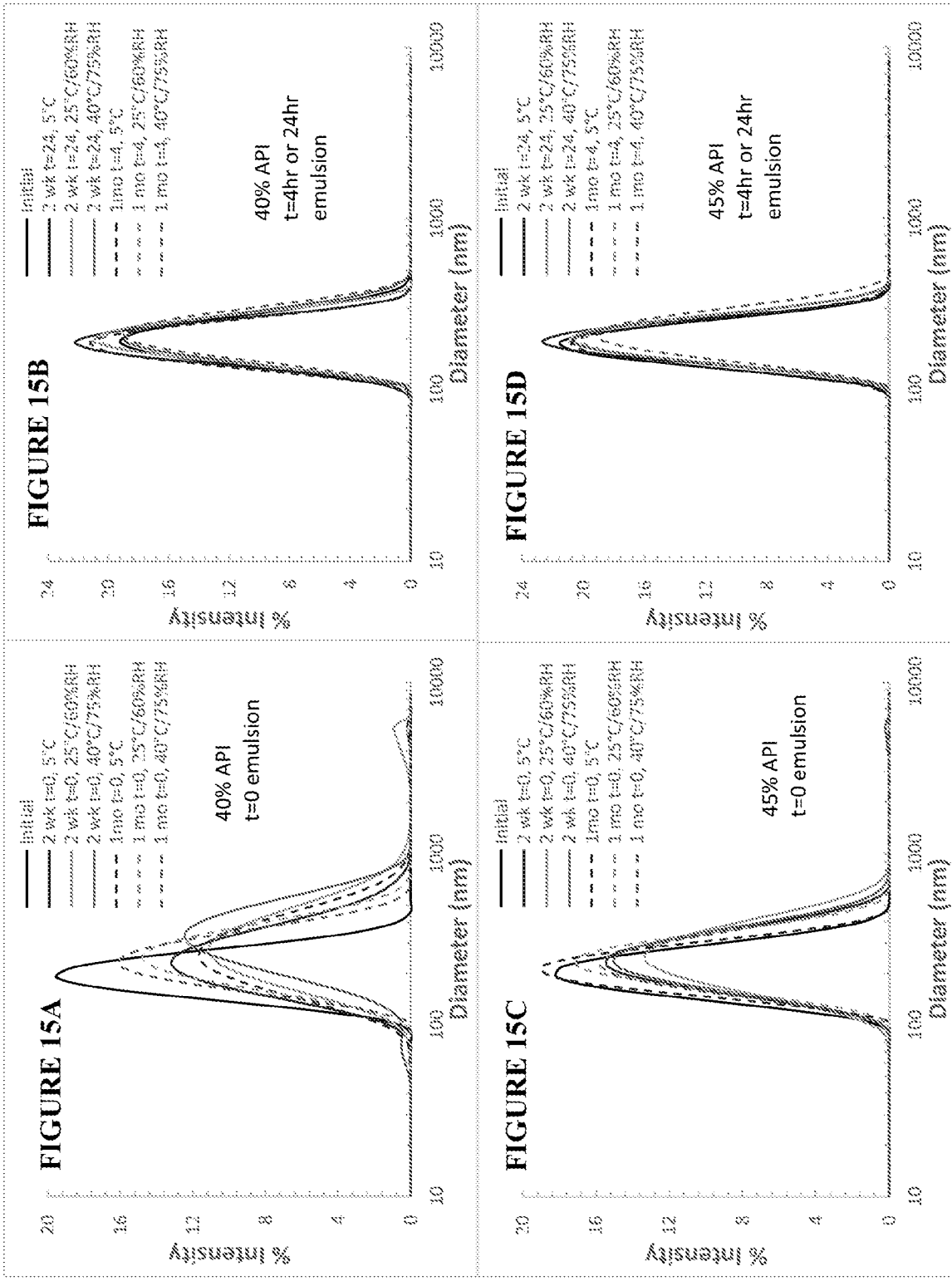

PHARMACEUTICAL COMPOSITIONS HAVING HIGH DRUG LOADINGS OF MEDIUM CHAIN TRIGLYCERIDES AND METHODS RELATED THERETO

FIELD OF THE INVENTION

This disclosure relates to pharmaceutical compositions comprising high drug loadings of medium chain triglycerides, as well as methods of making and methods of using such compositions.

BACKGROUND OF THE INVENTION

Medium Chain Triglycerides (MCTs) are comprised of fatty acids with chain length between 5-12 carbons. MCTs have been researched extensively and have known nutritional and pharmaceutical uses. MCTs having melting points which are liquid at room temperature. Further, MCTs are relatively small and are ionizable under physiological conditions, and are generally soluble in aqueous solutions.

When intended to be used as a pharmaceutical composition, it is often more desirable to prepare compositions of active ingredients that are present as a liquid at room temperature, such as MCTs, as a solid dosage form.

As such, there is a need in the art for solid dosage form compositions of MCTs, particularly at active ingredient to excipient levels (herein referred to as drug loading) sufficiently high for pharmaceutical use.

SUMMARY OF THE INVENTION

In one aspect, the disclosure relates to a solid pharmaceutical composition comprising a high drug loading of an active agent comprising an MCT, e.g., caprylic triglyceride; at least one surfactant; an adsorbent, and a film forming polymer. The composition may further include a co-surfactant. In some embodiments, the solid composition comprises at least two surfactants. In some embodiments, the active agent consists essentially of an MCT, e.g., caprylic triglyceride. In certain embodiments, the solid composition is a self-emulsifying, spray dried composition.

In certain aspects, the active agent comprises or consists essentially of an MCT which is present in an amount of at least about 35%, at least about 40%, between about 40% and about 65%, etc., by weight of the total composition. In certain embodiments, the MCT is caprylic triglyceride.

In other aspects, the at least one surfactant is selected from polyoxyl hydrogenated castor oil, polyoxyl stearate, polyoxyl hydroxystearate, lecithin, phosphatidylcholine, and combinations thereof. In certain embodiments, the solid composition comprises at least two surfactants, which may be selected from polyoxyl hydrogenated castor oil, polyoxyl stearate, polyoxyl hydroxystearate, lecithin, phosphatidylcholine, and combinations thereof. In certain embodiments, at least one of the at least two surfactants is a polyoxyl hydrogenated castor oil or polyoxyl stearate surfactant. The at least two surfactants may be present in a 2:1 to 1:1 ratio, relative to each other.

In certain aspects, the adsorbent is a silica compound, e.g., colloidal silicon dioxide (AEROSIL®, CAB-O-SIL®), amorphous silica gel (SYLOID®, SYLYSIA®), granulated silicon dioxide (AEROPERL®), silica aerogel, magnesium alumino metasilicates (NEUILIN®), calcium silicate (FLO-RITE®), and ordered mesoporous silicates.

In certain aspects, the film forming polymer may be polyvinylpyrrolidone (PVP), polyvinylpyrrolidone-vinyl acetate copolymer (PVP-VA), hydroxypropyl methylcellulose (HPMC), hydroxypropyl methylcellulose acetate succinate (HPMCAS), dextrans of varying molecular weights (e.g., 10000, 40000, 70000, 500000, etc.), etc. In certain embodiments, the film forming polymer is PVP or PVP-VA, in other embodiments the film forming polymer is PVP-VA.

In yet other aspects, the solid pharmaceutical composition of the disclosure may comprise spray dried particles having an average diameter of between about 5 µm and about 50 µm in diameter, between about 5 µm and about 30 µm in diameter, between about 5 µm and about 20 µm in diameter, between about 5 µm and about 10 µm in diameter, etc.

In other aspects, the solid pharmaceutical composition of the disclosure forms an emulsion in an aqueous use environment that is stable for at least about 4 hours at ambient conditions. In certain embodiments, the emulsions may have a mean droplet diameter of less than about 1000 nm, but greater than about 100 nm, e.g. between about 100 nm and 500 nm, between about 200 nm and about 300 nm, between about 160 nm and about 190 nm, etc.

In yet other aspects, the disclosure relates to methods of treating a disease or disorder associated with reduced cognitive function in a subject in need thereof, the method comprising administering to the subject a self-emulsifying, spray dried pharmaceutical composition of the disclosure in an amount effective to elevate ketone body concentrations in said subject to thereby treat said disease or disorder. In certain embodiments, the disease or disorder associated with reduced cognitive function is selected from Alzheimer's disease and Age-Associated Memory Impairment.

In other aspects, the disclosure relates to methods of making the self-emulsifying, spray dried pharmaceutical composition of the disclosure. In one embodiment, the film-forming polymer is added to a solution for forming the spray dried pharmaceutical composition prior to the adsorbent.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

BRIEF DESCRIPTION OF THE DRAWINGS

FIG. 1 illustrates an exemplary process for manufacturing pharmaceutical compositions of the disclosure.

FIG. 5 illustrates the DSC thermogram overlay of 40% and 45% API spray dried compositions, in accordance with embodiments of the disclosure.

FIGS. 6A-6B illustrate SEM Images of 40% (panel A) and 45% (panel B) API spray dried composition particles at 500× magnification, in accordance with embodiments of the disclosure.

FIGS. 12A-12C illustrate particle size distribution of 40% (Panel A) and 45% (Panel B) API spray dried composition particles at 2 weeks, along with data table (Panel C), in accordance with embodiments of the disclosure.

FIGS. 14A-14C illustrate particle size distribution of 40% (Panel A) and 45% (Panel B) API Spray Dried composition particles after 1 month stability storage, along with data table (Panel C), in accordance with embodiments of the disclosure.

FIGS. 15A-15D illustrate droplet size distribution for emulsions formed from 40% (Panel A, initial; Panel B, after 4 to 24 hours at ambient conditions) and 45% (Panel C, initial; Panel D, after 4 to 24 hours at ambient conditions) API spray dried compositions, in accordance with embodiments of the disclosure.

DETAILED DESCRIPTION OF THE INVENTION

Figure 2A:
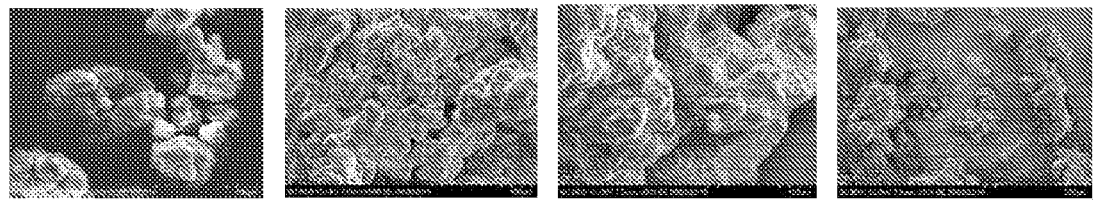
FIG. 2A-2C illustrates SEM images of 60% (Panel A), 50% (Panel B), and 60% (Panel C) API spray dried composition particles at 500× magnification, in accordance with embodiments of the disclosure.

By way of background, Medium Chain Triglycerides ("MCT"s) are metabolized differently from the more common Long Chain Triglycerides (LCTs). In particular, when compared to LCTs, MCTs are more readily digested to release medium chain fatty acids (MCFAs), which exhibit increased rates of portal absorption, and undergo obligate oxidation. The small size and decreased hydrophobicity of MCTs increases the rate of digestion and absorption relative to LCTs. When MCTs are ingested, they are first processed by lipases, which cleave the fatty acid chains from the glycerol backbone. Some lipases in the pre-duodenum preferentially hydrolyze MCTs over LCTs, and the released MCFAs are then partly absorbed directly by the stomach mucosa. Those MCFAs which are not absorbed in the stomach are absorbed directly into the portal vein and not packaged into lipoproteins. Since blood transports much more rapidly than lymph, MCFAs quickly arrive at the liver. In the liver MCFAs undergo obligate oxidation.

In contrast, long chain fatty acids (LCFAs) derived from normal dietary fat are re-esterified into LCTs and packaged into chylomicrons for transport in the lymph. This greatly slows the metabolism of LCTs relative to MCTs. In the fed state LCFAs undergo little oxidation in the liver, due mainly to the inhibitory effects of malonyl-CoA. When conditions favor fat storage, malonyl-CoA is produced as an intermediate in lipogenesis. Malonyl-CoA allosterically inhibits carnitine palmitoyltransferase I, and thereby inhibits LCFA transport into the mitochondria. This feedback mechanism prevents futile cycles of lipolysis and lipogenesis.

MCFAs are, to a large extent, immune to the regulations that control the oxidation of LCFAs. MCFAs enter the mitochondria without the use of carnitine palmitoyltransferase I, therefore MCFAs by-pass this regulatory step and are oxidized regardless of the metabolic state of the organism. Importantly, since MCFAs enter the liver rapidly and are quickly oxidized, large amounts of ketone bodies are readily produced from MCFAs. As such, a large oral dose of MCTs (e.g., about 20 mL to 40 mL) will result in sustained hyperketonemia.

In certain aspects of the disclosure it has been found that bioavailability of MCTs can be increased by emulsification of the pharmaceutical composition used to deliver the MCTs prior to or upon delivery of the pharmaceutical composition to a patient. Without intending to be limited, emulsification of lipids increases the surface area for action by lipases, resulting in more rapid hydrolysis and release of medium chain fatty acids in vivo.

The present disclosure generally relates to solid pharmaceutical compositions comprising a high loading of an active agent comprising at least one MCT, and methods of making and using such compositions. In certain embodiments, the MCT is caprylic triglyceride, as described herein.

In certain aspects, the solid pharmaceutical compositions comprise spray dried particles for reconstitution to an emulsion ("self-emulsifying") in an aqueous use environment, e.g., in water or when administered to an aqueous use environment. In certain embodiments, the spray dried particles comprise nano-adsorbents which provide a high surface area solid support for the active agent comprising the at least one MCT during formation of the spray dried particles, and thereafter release the at least one MCT to solution during emulsification.

In certain aspects, the solid pharmaceutical compositions of the disclosure are a self-emulsifying, spray dried pharmaceutical composition comprising a high drug load of an active agent comprising an MCT (e.g., caprylic triglyceride), at least one surfactant, an adsorbent, and a film forming polymer. In certain embodiments, the pharmaceutical compositions may comprise at least two surfactants. The pharmaceutical compositions may also include a co-surfactant. The pharmaceutical compositions may further include additional excipients such as flavor enhancers and/or taste masking agents. The pharmaceutical compositions may comprise the components in amounts as described herein.

The solid pharmaceutical compositions of the disclosure provide small, spray dried particles that form a stable emulsion on reconstitution in an aqueous use environment. The pharmaceutical compositions comprise spray dried particles having an average particle size of less than about 50 µm in diameter, between about 5 µm and about 50 µm in diameter, between about 5 µm and about 30 µm in diameter, between about 5 µm and about 20 µm in diameter, between about 5 µm and about 10 µm in diameter, etc.

In certain aspects, the pharmaceutical compositions of the disclosure provide spray dried particles that form flowable powders. In certain embodiments, the flowable powders exhibit a Carr Index of less than about 37%, and/or a Hausner Ratio of less than about 1.59.

Reference to an "aqueous use environment" can mean in vivo fluids, such as the gastrointestinal tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or an in vitro environment of a test solution, such as water, phosphate buffered saline (PBS), a Model Fasted Duodenal (MFD) solution, or a solution to model the fed state. An appropriate PBS solution is an aqueous solution comprising 20 mM sodium phosphate (Na2HPO4), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. An appropriate solution to model the fed state is the same PBS solution wherein additionally is present 29.2 mM sodium taurocholic acid and 5.6 mM of 1-palmitoyl-2-oleylsn-glycero-3-phosphocholine.

As used herein, "administration" to an aqueous use environment includes an in vivo use environment, such as the gastrointestinal tract, delivery by ingestion or swallowing or other such means to deliver the pharmaceutical composition, as understood by those skilled in the art. See for example, *Remington: The Science and Practice of Pharmacy,* 20th *Edition* (2000). Where the aqueous use environment is in vitro, "administration" refers to placement or delivery of the pharmaceutical composition in the in vitro test medium.

As described herein, the pharmaceutical compositions of the disclosure are "self-emulsifying." The term "self-emulsifying" refers to a composition which, when diluted with water or other aqueous medium and gently mixed, yields a stable oil/water emulsion with a mean droplet diameter of less than about 5 μm, but greater than about 100 nm, and which is generally polydisperse. Such an emulsion is stable, meaning there is no visibly detectable phase separation and that there is no visibly detectable crystallization. "Gentle mixing" as used above is understood in the art to refer to the formation of an emulsion by gentle hand (or machine) mixing, such as by repeated inversions on a standard laboratory mixing machine. High shear mixing is not required to form the emulsion. Such self-emulsifying compositions generally emulsify nearly spontaneously when introduced into the human (or other animal) gastrointestinal tract.

As discussed above, the pharmaceutical compositions of the disclosure form stable emulsions on reconstitution in an aqueous use environment, e.g., in water or when administered in vivo. By way of example, the emulsions may be stable at ambient conditions for at least about 10 minutes, at least about 20 minutes, at least about 30 minutes, at least about 45 minutes at least about 1 hour, at least about 2 hours, at least about 4 hours, at least about 5 hours, at least about 24 hours, etc. In certain embodiments, the emulsion formed does not phase separate for the duration of stability. In certain embodiments, the emulsions may have a mean droplet diameter of less than about 1000 nm, but greater than about 100 nm, e.g. between about 100 nm and 500 nm, between about 200 nm and about 300 nm, etc.

In certain embodiments, the emulsion formed may be stable at stomach pH, e.g., at a pH of about 1 to about 3, about 1.2 to 2.9, etc. In certain embodiments, the emulsion formed may be stable at intestinal and/or colon pH, e.g., at a pH of about 5 to about 7, about 5.5 to about 6.9, etc. In certain embodiments, the emulsion formed may begin to break down or phase separate at stomach pH after about ½ to about 1 hour, but does not release the encapsulated MCT until intestinal or colon pH. In this regard, without intending to be limited by theory, in-vitro digestion assays indicate that encapsulated MCT is released from emulsion at intestinal and/or colon pH, which is the primary location of lipid digestion enzymes. In accordance with certain aspects of the disclosure, preferential release of MCT in the intestines and/or colon rather than the stomach may increase bioavailability of the MCT given the location of lipid digestion enzymes in these areas.

Again, without intending to be limited by theory, preferential release of MCT in the intestines and/or colon may provide reduced stomach upset and related adverse events as compared to standard administration of non-formulated MCT oil. Further, the improved bioavailability of the MCT may generally lead to increased ketone body production in vivo, as compared to standard administration of non-formulated MCT oil.

In certain embodiments, the pharmaceutical compositions may include a high drug load of an active agent comprising or consisting essentially of at least one MCT, such as caprylic triglyceride, of at least about 30% by weight of the total composition, at least about 35% of the total composition, at least about 40% by weight of the total composition, about 30% by weight of the total composition to about 65% by weight of the total composition, about 30% by weight of the total composition to about 60% by weight of the total composition, about 35% by weight of the total composition to about 60% by weight of the total composition about 40% by weight of the total composition to about 55% by weight of the total composition, about 40% by weight of the total composition to about 50% by weight of the total composition, etc.

As used herein, unless otherwise specified, "% by weight" refers to "% by weight of the total composition".

In certain aspects, the solid pharmaceutical compositions of the disclosure may comprise a high drug loading of an active agent comprising or consisting essentially of at least one MCT, at least one or two surfactants, an adsorbent, and a film forming polymer. The pharmaceutical compositions may also include a co-surfactant.

In certain aspects of the disclosure, MCTs refer to any glycerol molecule ester-linked to three fatty acid molecules, each fatty acid molecule having a carbon chain of 5-12 carbons. In certain embodiments, the pharmaceutical compositions may comprise an MCT represented by the following general formula:

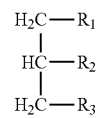

wherein $R_1$, $R_2$ and $R_3$ are fatty acids having 5-12 carbons in the carbon backbone esterified to the glycerol backbone.

The MCTs of the disclosure may be prepared by any process known in the art, such as direct esterification, rearrangement, fractionation, transesterification, or the like. Sources of the MCT include any suitable source, semi-synthetic, synthetic or natural. Examples of natural sources of MCT include plant sources such as coconuts and coconut oil, palm kernels and palm kernel oils, and animal sources such as milk from any of a variety of species, e.g., goats. For example, the lipids may be prepared by the rearrangement of a vegetable oil such as coconut oil. The length and distribution of the chain length may vary depending on the source oil. For example, MCT containing 1-10% C6, 30-60% C8, 30-60% C10, 1-10% C10 are commonly derived from palm and coconut oils.

In accordance with certain embodiments of the disclosure, the solid pharmaceutical compositions of the disclosure may comprise an active agent comprising or consisting essentially of MCTs that have greater than about 95%, e.g., 98%, C8 at $R_1$, $R_2$ and $R_3$, and are herein referred to as caprylic triglyceride ("CT"). Exemplary sources of CT include MIGLYOL® 808 or NEOBEE® 895. In certain aspects, CT may be obtained from coconut or palm kernel oil, made by semi-synthetic esterification of octanoic acid to glycerin, etc.

In other embodiments, the solid pharmaceutical compositions may comprise an active agent comprising or consisting essentially of MCTs wherein $R_1$, $R_2$, and $R_3$ are fatty acids containing a six-carbon backbone (tri-C6:0). Tri-C6:0 MCT are absorbed very rapidly by the gastrointestinal tract in a number of animal model systems. The high rate of absorption results in rapid perfusion of the liver, and a potent ketogenic response. In another embodiment, the pharmaceutical compositions may comprise an active agent comprising or consisting essentially of MCTs wherein $R_1$, $R_2$, and $R_3$ are fatty acids containing an eight-carbon backbone (tri-C8:0). In another embodiment, the pharmaceutical compositions may comprise an active agent comprising or consisting essentially of MCTs wherein $R_1$, $R_2$, and $R_3$ are fatty acids containing a ten-carbon backbone (tri-C10:0). In another embodiment, the pharmaceutical compositions may comprise MCTs wherein $R_1$, $R_2$, and $R_3$ are a mixture of C8:0 and C10:0 fatty acids. In another embodiment, the pharmaceutical compositions may comprise an active agent comprising or consisting essentially of MCTs wherein $R_1$, $R_2$ and $R_3$ are a mixture of C6:0, C8:0, C10:0, and C12:0 fatty acids. In another embodiment, the pharmaceutical compositions may comprise an active agent comprising or consisting essentially of MCTs wherein greater than 95% of $R_1$, $R_2$ and $R_3$ are 8 carbons in length. In yet another embodiment, the pharmaceutical compositions may comprise an active agent comprising or consisting essentially of MCTs wherein the $R_1$, $R_2$, and $R_3$ carbon chains are 6-carbon or 10-carbon chains In another embodiment, the pharmaceutical compositions may comprise an active agent comprising or consisting essentially of MCTs wherein about 50% of $R_1$, $R_2$ and $R_3$ are 8 carbons in length and about 50% of $R_1$, $R_2$ and $R_3$ 10 carbons in length. In one embodiment, the pharmaceutical compositions may comprise an active agent comprising or consisting essentially of MCTs wherein $R_1$, $R_2$ and $R_3$ are 6, 7, 8, 9, 10 or 12 carbon chain length, or mixtures thereof.

As discussed above, in certain embodiments, the solid pharmaceutical composition may include at least one or two surfactants. Without intending to be limited, the surfactants may generally facilitate emulsification of the high drug loading of MCT. By way of example, the surfactant(s) may be selected from at least one of polyoxyl hydrogenated castor oil (e.g., KOLLIPHOR® RH 40), polyoxyl stearate (e.g., Gelucire 48/16), polyoxyl hydroxystearate, lecithin, phosphatidylcholine (e.g., PHOSPHOLIPON® 90G), and combinations thereof. In certain embodiments, at least one of the surfactants is a polyoxyl hydrogenated castor oil (e.g., a polyoxyl hydrogenated castor oil derived from hydrogenated castor oil and ethylene oxide such as KOLLIPHOR® RH 40) or a polyoxyl hydroxystearate surfactant. Any suitable amount of surfactant may be used to achieve the desired emulsification of the MCT. In certain embodiments, the surfactants may each be present in an amount at least about 2.0%, at least about 2.5%, between about 2.0 wt % and about 10.0 wt %, between about 2.5 wt % and about 6.0 wt %, between about 2.5 wt % and about 3.0 wt %, etc. In certain embodiments, when at least two surfactants are present, the surfactants may be present at a 1:1 to 2:1 ratio, a 1:1 ratio, etc. (relative to each other).

In certain aspects, the solid pharmaceutical compositions of the disclosure also include at least one co-surfactant. The co-surfactant can be any suitable co-surfactant known in the art for facilitating surfactant activity to provide desired emulsion formation and stabilization. In certain embodiments, the co-surfactant may be a glycerol ester or propylene glycol ester, such a glycerol ester or propylene glycol ester of caprylic acid, lauric acid, or stearic acid, e.g., glyceryl caprylate, glyceryl monocaprylate, glyceryl monooleate, propylene glycol dicaprylate/dicaprate, propylene glycol monolaurate, and combinations thereof. In certain aspects, the co-surfactant may be a blend of glycerol esters of caprylic acid, e.g., with a monoester content of at least about 80% (e.g., IMWITOR® 308 or CAPMUL® 808G). Any suitable amount of co-surfactant may be used to achieve the desired activity with the surfactants. In certain embodiments, the co-surfactants may be present at a 3:1 to 1:1 ratio, a 2:1 ratio, etc. (relative to each surfactant). In certain embodiments, the co-surfactants may each be present in an amount ranging from about 2.0 wt % to about 10.0 wt %, from about 2.5 wt % to about 6.0 wt %, from about 3.0 wt % to about 6.0 wt %, etc.

In certain aspects, the solid pharmaceutical compositions of the disclosure also include an adsorbent. In certain embodiments, the adsorbent is a silica compound, e.g., colloidal silicon dioxide (AEROSIL®, CAB-O-SIL®), amorphous silica gel (SYLOID®, SYLYSIA®), granulated silicon dioxide (AEROPERL®), silica aerogel, magnesium alumino metasilicates (NEUILIN®), calcium silicate (FLORITE®), and ordered mesoporous silicates. The adsorbent may be present in the composition in any suitable amount to provide the desired flowability. For example, in certain embodiments, the adsorbent may be present in an amount of at least about 2% by weight, at least about 5% by weight, at least about 10% by weight, at least about 15% by weight, at least about 20% by weight, at least about 25% by weight, at least about 30% by weight, between about 2.0% and about 30% by weight, between about 2.0% and about 20% by weight, etc.

In certain aspects, the solid pharmaceutical compositions of the disclosure include a film forming polymer. The film forming polymer may be any suitable film forming polymer known in the art which provides the desired spray dried particle formation. By way of example, the film forming polymer may be PVP (povidone, polyvinylpyrrolidone); PVA (polyvinylalcohol); polyvinylpyrrolidone-vinyl acetate copolymer (PVP-VA, copovidone),; dextrans of varying molecular weights(e.g., 10000, 40000, 70000, 500000, etc., grades 1-70); hydroxypropyl methylcellulose (HPMC, hypromellose), hydroxypropyl methylcellulose acetate succinate (HPMCAS, hypromellose Acetate Succinate); hydroxypropyl methylcellulose phthalate (HPMCP, hypromellose phthalate); cellulose acetate phthalate (CAP); hydroxypropyl cellulose (HPC); methylcellulose (MC); hydroxyethylcellulose (HEC); carboxymethylcellulose (CMC); ethyl cellulose (GRAS 470); acacia; chitosan; gelatin; polyethylene glycol of varying molecular weights (PEG); polyethylene oxide of varying molecular weights (PEO); xanthan gum; carrageenan; locust bean gum; potassium or sodium alginate; starch; agar, etc. In certain embodiments, the film forming polymer may be polyvinylpyrrolidone (PVP), polyvinylpyrrolidone-vinyl acetate copolymer (PVP-VA), hydroxypropyl methylcellulose (HPMC), hydroxypropyl methylcellulose acetate succinate (HPMCAS), dextrans of varying molecular weights (e.g., 10000, 40000, 70000, 500000, etc.), etc. In certain embodiments, the film forming polymer is PVP or PVP-VA, in other embodiments the film forming polymer is PVP-VA. The film forming polymer may be present in amounts sufficient to provide desired spray dried particle formation. For example, in certain embodiments, the film forming polymer may be present in an amount of at least about 5% by weight, at least about 8% by weight, at least about 10% by weight, at least about 15% by weight, at least about 20% by weight, at least about 25% by weight, at least about 30% by weight, between about 8% by weight and about 30% by weight, etc.

In certain embodiments, the solid pharmaceutical compositions may comprise a high drug loading of an active agent comprising or consisting essentially of at least one MCT such as caprylic triglyceride, at least one or two surfactants, an adsorbent, and a film forming polymer. The solid pharmaceutical compositions may further comprise a co-surfactant, as described herein. In certain embodiments, at least one of the surfactants may be a polyoxyl hydrogenated castor oil or polyoxyl hydroxystearate surfactant, which present in an amount of at least 2.5% by weight. In certain embodiments, the adsorbent may be a silica compound such as colloidal silicon dioxide, which may be present in an amount of at least about 2% by weight. In certain embodiments, the film forming polymer is polyvinylpyrrolidone (PVP) or polyvinylpyrrolidone-vinyl acetate copolymer (PVP-VA), in other embodiments the film forming polymer is PVP-VA, which may be present in an amount of at least about 8% by weight of the total composition.

Any suitable method for making the pharmaceutical compositions of the disclosure may be used. In certain aspects of the disclosure, it has been found that reproducibility, particle size and morphology, and yield may be controlled by modifying manufacturing process and spray drying conditions.

For instance, with reference to FIG. 1, an exemplary spray dry process 100 for manufacture of pharmaceutical compositions of the disclosure is illustrated. At step 102, a lipid mixture is prepared wherein MCT and the at least two surfactants are added to an appropriate lipid mixture preparation vessel. The lipid mixture is agitated and heated to an appropriate temperature to dissolve the components, e.g., room temperature to about 100° C., more particularly about 70° C. Thereafter, any co-surfactant may be added, and the lipid mixture may be mixed while maintaining temperature for sufficient time to allow all components to dissolve, e.g., for at least 30-120 minutes, more particularly about 90 minutes. The lipid mixture is then allowed to cool to room temperature once all components are dissolved.

At step 104, in a separate solution preparation vessel, solvent is added, e.g., purified water, and agitation is started. At step 106, any optional film forming polymer is added to the solvent in the solution preparation vessel and mixed with agitation for sufficient time to allow the film forming polymer to dissolve in the solvent, e.g., for at least 30-120 minutes. At step 108, the adsorbent is added to the solution preparation vessel and mixed with agitation until the adsorbent is fully wetted, e.g., for at least 15-120 minutes. In other embodiments, step 106 is not performed (i.e., no optional film forming polymer is added), steps 106 and 108 are performed simultaneously, or step 108 is performed prior to step 106. In this regard, in certain embodiments, it was found that manufacturing processability may be improved if any optional film forming polymer is dissolved in solvent, e.g., water or ethanol, prior to wetting of the adsorbent in the solvent. In certain instances it was found that the solution formed a thick gel that was difficult to spray dry if any optional film forming polymer was added after the flow agent was wetted with solvent.

At step 110, the lipid mixture from step 102 is added with agitation to the mixture in the solution vessel from step 108. The lipid mixture vessel may be rinsed with solvent to ensure that all lipid mixture is transferred to the solution vessel. Alternatively, the solution mixture (adsorbent/film forming polymer) may be added to the lipid mixture vessel. In another embodiment, the solvent, optional film forming polymer, and adsorbent may be added directly to the lipid mixture vessel. The solution is mixed until all components form a final solution preparation/emulsion, e.g., for at least 10-120 minutes. The final solution preparation/emulsion from step 110 is then spray dried at step 112.

Any suitable spray drying conditions may be used to obtain the desired particle morphology. For instance, at a bench scale, an atomization pressure of about 10-50 PSI, a feed rate of about 5-40 ml/min, and a solids loading of about 15-25 wt % or higher may be used. An inlet temperature of about 100° C. to about 175° C., and an outlet temperature of about 50° C. to about 65° C. may be used. Continuous mixing may be employed for the duration of the spray drying run to keep the adsorbent suspended. Exemplary methods may be performed using a laboratory scale spray dryer with a 150-kg/hr drying-gas flow-rate capacity. In accordance with the methods of the disclosure, yields may be between 75-105%.

In certain aspects, the disclosure relates to methods of treating a disease or disorder associated with reduced cognitive function in a subject in need thereof, the method comprising administering to the subject a pharmaceutical composition of the disclosure in an amount effective to elevate ketone body concentrations in said subject to thereby treat said disease or disorder. In certain embodiments, the pharmaceutical composition of the disclosure may be administered outside of the context of a ketogenic diet. For instance, in the context of the present disclosure, carbohydrates may be consumed at the same time as pharmaceutical compositions disclosed herein.

In accordance with certain aspects of the disclosure, diseases and disorders associated with reduced cognitive function include h Age-Associated Memory Impairment (AAMI), Alzheimer's Disease (AD), Parkinson's Disease, Friedreich's Ataxia (FRDA), GLUT1-deficient Epilepsy, Leprechaunism, and Rabson-Mendenhall Syndrome, Coronary Arterial Bypass Graft (CABG) dementia, anesthesia-induced memory loss, Huntington's Disease, and many others.

In another embodiment, the patient has or is at risk of developing disease-related reduced cognitive function caused by reduced neuronal metabolism, for example, reduced cognitive function associated with Alzheimer's Disease (AD), Parkinson's Disease, Friedreich' s Ataxia (FRDA), GLUT1-deficient Epilepsy, Leprechaunism, and Rabson-Mendenhall Syndrome, Coronary Arterial Bypass Graft (CABG) dementia, anesthesia-induced memory loss, Huntington's Disease, and many others.

As used herein, reduced neuronal metabolism refers to all possible mechanisms that could lead to a reduction in neuronal metabolism. Such mechanisms include, but are not limited to mitochondrial dysfunction, free radical attack, generation of reactive oxygen species (ROS), ROS-induced neuronal apoptosis, defective glucose transport or glycolysis, imbalance in membrane ionic potential, dysfunction in calcium flux, and the like.

According to the present invention, high blood ketone levels will provide an energy source for brain cells that have compromised glucose metabolism, leading to improved performance in cognitive function. As used herein, "subject" and "patient" are used interchangeably, and refer to any mammal, including humans that may benefit from treatment of disease and conditions associated with or resulting from reduced neuronal metabolism.

"Effective amount" refers to an amount of a compound, material, or pharmaceutical composition, as described herein that is effective to achieve a particular biological result. Effectiveness for treatment of the aforementioned conditions may be assessed by improved results from at least one neuropsychological test. These neuropsychological tests are known in the art and include Clinical Global Impression of Change (CGIC), Rey Auditory Verbal Learning Test (RAVLT), First-Last Names Association Test (FLN), Telephone Dialing Test (TDT), Memory Assessment Clinics Self-Rating Scale (MAC-S), Symbol Digit Coding (SDC), SDC Delayed Recall Task (DRT), Divided Attention Test (DAT), Visual Sequence Comparison (VSC), DAT Dual Task (DAT Dual), Mini-Mental State Examination (MMSE), and Geriatric Depression Scale (GDS), among others.

The term "cognitive function" refers to the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness. "Enhanced cognitive function" or "improved cognitive function" refers to any improvement in the special, normal, or proper physiologic activity of the brain, including, without limitation, at least one of the following: mental stability, memory/recall abilities, problem solving abilities, reasoning abilities, thinking abilities, judging abilities, capacity for learning, perception, intuition, attention, and awareness, as measured by any means suitable in the art. "Reduced cognitive function" or "impaired cognitive function" refers to any decline in the special, normal, or proper physiologic activity of the brain.

In another embodiment, the methods of the present invention further comprise determination of the patients' genotype or particular alleles. In one embodiment, the patient's alleles of the apolipoprotein E gene are determined. It has been found that non-E4 carriers performed better than those with the E4 allele when elevated ketone body levels were induced with MCT. Also, those with the E4 allele had higher fasting ketone body levels and the levels continued to rise at the two hour time interval. Therefore, E4 carriers may require higher ketone levels or agents that increase the ability to use the ketone bodies that are present.

In one embodiment, the pharmaceutical compositions of the disclosure are administered orally. Therapeutically effective amounts of the therapeutic agents can be any amount or dose sufficient to bring about the desired effect and depend, in part, on the severity and stage of the condition, the size and condition of the patient, as well as other factors readily known to those skilled in the art. The dosages can be given as a single dose, or as several doses, for example, divided over the course of several weeks, as discussed elsewhere herein.

The pharmaceutical compositions of the disclosure, in one embodiment, are administered in a dosage required to increase blood ketone bodies to a level required to treat and/or prevent the occurrence of any disease- or age-associated cognitive decline, such as AD, AAMI, and the like. Appropriate dosages may be determined by one of skill in the art.

In one embodiment, oral administration of a pharmaceutical composition of the disclosure results in hyperketonemia. Hyperketonemia, in one embodiment, results in ketone bodies being utilized for energy in the brain even in the presence of glucose. Additionally, hyperketonemia results in a substantial (39%) increase in cerebral blood flow (Hasselbalch, S. G., et al., Changes in cerebral blood flow and carbohydrate metabolism during acute hyperketonemia, *Am J Physiol*, 1996, 270:E746-51). Hyperketonemia has been reported to reduce cognitive dysfunction associated with systemic hypoglycemia in normal humans (Veneman, T., et al., Effect of hyperketonemia and hyperlacticacidemia on symptoms, cognitive dysfunction, and counterregulatory hormone responses during hypoglycemia in normal humans, *Diabetes*, 1994, 43:1311-7). Please note that systemic hypoglycemia is distinct from the local defects in glucose metabolism that occur in any disease- or age-associated cognitive decline, such as AD, AAMI, and the like.

Administration can be on an as-needed or as-desired basis, for example, once-monthly, once-weekly, daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the patient or otherwise contacted with or admixed with daily feed or food.

The pharmaceutical compositions provided herein are, in one embodiment, intended for "long term" consumption, sometimes referred to herein as for 'extended' periods. "Long term" administration as used herein generally refers to periods in excess of one month. Periods of longer than two, three, or four months comprise one embodiment of the instant invention. Also included are embodiments comprising more extended periods that include longer than 5, 6, 7, 8, 9, or 10 months. Periods in excess of 11 months or 1 year are also included. Longer terms use extending over 1, 2, 3 or more years are also contemplated herein. "Regular basis" as used herein refers to at least weekly, dosing with or consumption of the compositions. More frequent dosing or consumption, such as twice or thrice weekly are included. Also included are regimens that comprise at least once daily consumption. The skilled artisan will appreciate that the blood level of ketone bodies, or a specific ketone body, achieved may be a valuable measure of dosing frequency. Any frequency, regardless of whether expressly exemplified herein, that allows maintenance of a blood level of the measured compound within acceptable ranges can be considered useful herein. The skilled artisan will appreciate that dosing frequency will be a function of the composition that is being consumed or administered, and some compositions may require more or less frequent administration to maintain a desired blood level of the measured compound (e.g., a ketone body).

Administration can be carried out on a regular basis, for example, as part of a treatment regimen in the patient. A treatment regimen may comprise causing the regular ingestion by the patient of a pharmaceutical composition of the disclosure in an amount effective to enhance cognitive function, memory, and behavior in the patient. Regular ingestion can be once a day, or two, three, four, or more times per day, on a daily or weekly basis. Similarly, regular administration can be every other day or week, every third day or week, every fourth day or week, every fifth day or week, or every sixth day or week, and in such a regimen, administration can be multiple times per day. The goal of regular administration is to provide the patient with optimal dose of a pharmaceutical composition of the disclosure, as exemplified herein.

Dosages of the inventive compositions, such as, for example, those comprising MCT, may be administered in an effective amount to increase the cognitive ability of patients afflicted with diseases of reduced neuronal metabolism, such as in patients with any disease- or age-associated cognitive decline, such as, AD, AAMI, and the like.

In one embodiment, the inventive compositions result in elevating ketone concentrations in the body, and in this embodiment, the compositions are administered in an amount that is effective to induce hyperketonemia. In one embodiment, hyperketonemia results in ketone bodies being utilized for energy in the brain.

In one embodiment, the composition increases the circulating concentration of at least one type of ketone body in the mammal or patient. In one embodiment, the circulating ketone body is D-beta-hydroxybutyrate. The amount of circulating ketone body can be measured at a number of times post administration, and in one embodiment, is measured at a time predicted to be near the peak concentration in the blood, but can also be measured before or after the predicted peak blood concentration level. Measured amounts at these off-peak times are then optionally adjusted to reflect the predicted level at the predicted peak time. In one embodiment, the predicted peak time is at about two hours. Peak circulating blood level and timing can vary depending on factors known to those of skill in the art, including individual digestive rates, co-ingestion or pre- or post-ingestion of foods, drinks, etc., as known to one of skill in the art. In one embodiment, the peak blood level reached of D-beta-hydroxybutyrate is between about 0.05 millimolar (mM) to about 50 mM. Another way to determine whether blood levels of D-beta-hydroxybutyrate are raised to about 0.05 to about 50 mM is by measurement of D-beta-hydroxybutyrate urinary excretion a range in the range of about 5 mg/dL to about 160 mg/dL. In other embodiments, the peak blood level is raised to about 0.1 to about 50 mM, from about 0.1 to about 20 mM, from about 0.1 to about 10 mM, to about 0.1 to about 5 mM, more preferably raised to about 0.15 to about 2 mM, from about 0.15 to about 0.3 mM, and from about 0.2 to about 5 mM, although variations will necessarily occur depending on the composition and host, for example, as discussed above. In other embodiments, the peak blood level reached of D-beta-hydroxybutyrate will be at least about 0.05 mM, at least about 0.1 mM, at least about 0.15 mM, at least about 0.2 mM, at least about 0.5 mM, at least about 1 mM, at least about 1.5 mM, at least about 2 mM, at least about 2.5 mM, at least about 3 mM, at least about 4 mM, at least about 5 mM, at least about 10 mM, at least about 15 mM, at least about 20 mM, at least about 30 mM, at least about 40 mM, and at least about 50 mM.

Effective amount of dosages of compounds for the inventive compositions, i.e., compounds capable of elevating ketone body concentrations in an amount effective for the treatment of or prevention of loss of cognitive function caused by reduced neuronal metabolism will be apparent to those skilled in the art. As discussed herein above, such effective amounts can be determined in light of disclosed blood ketone levels. Where the compound capable of elevating ketone body concentrations is MCT, the MCT dose, in one embodiment, is in the range of about 0.05 g/kg/day to about 10 g/kg/day of MCT. In other embodiments, the dose will be in the range of about 0.25 g/kg/day to about 5 g/kg/day of MCT. In other embodiments, the dose will be in the range of about 0.5 g/kg/day to about 2 g/kg/day of MCT. In other embodiments, the dose will be in the range of about 0.1 g/kg/day to about 2 g/kg/day. In other embodiments, the dose of MCT is at least about 0.05 g/kg/day, at least about 0.1 g/kg/day, at least about 0.15 g/kg/day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, and at least about 50 g/kg/day.

Convenient unit dosage containers and/or compositions include sachets or containers of spray dried particles, tablets, capsules, lozenges, troches, hard candies, nutritional bars, nutritional drinks, metered sprays, creams, and suppositories, among others. The compositions may be combined with a pharmaceutically acceptable excipient such as gelatin, oil(s), and/or other pharmaceutically active agent(s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with antioxidants, compounds that enhance the efficiency of glucose utilization, and mixtures thereof.

The daily dose of MCT can also be measured in terms of grams of MCT per kg of body weight (BW) of the mammal. The daily dose of MCT can range from about 0.01 g/kg to about 10.0 g/kg BW of the mammal. Preferably, the daily dose of MCT is from about 0.1 g/kg to about 5 g/kg BW of the mammal. More preferably, the daily dose of MCT is from about 0.2 g/kg to about 3 g/kg of the mammal. Still more preferably, the daily dose of MCT is from about 0.5 g/kg to about 2 g/kg of the mammal In some embodiments, the inventive compounds may be co administered with carbohydrate, or be co-formulated with carbohydrate. Carbohydrate can include more than one type of carbohydrate. Appropriate carbohydrates are known in the art, and include simple sugars, such as glucose, fructose, sucrose, and the like, from conventional sources such as corn syrup, sugar beet, and the like. If co-formulated, the amount of carbohydrate to use can include at least about 0.1 g, at least about 1g, at least about 10 g, at least about 50 g, at least about 100 g, at least about 150 g, at least about 200 g, at least about 250 g, at least about 300 g, at least about 400 g. Amounts of carnitine can be at least about 1 g, at least about 50 g, at least about 100 g. The compositions can comprise from about 15% to about 40% carbohydrate, on a dry weight basis. Sources of such carbohydrates include grains or cereals such as rice, corn, sorghum, alfalfa, barley, soybeans, canola, oats, wheat, or mixtures thereof. The compositions also optionally comprise other components that comprise carbohydrates such as dried whey and other dairy products or by-products.

EXAMPLES

The following examples are provided for illustrative purposes only and are not intended to limit the scope of the invention.

Example 1

Spray Dried Powder Compositions

Exemplary spray dried powder compositions were prepared, as described herein and reflected in Tables 1-1A and I-1B below.

TABLE 1-1A

| | Exemplary Compositions | | | | | | |
|---|---|---|---|---|---|---|---|
| | F-1 | F-2 | F-3 | F-4 | F-5 | F-6 | F-7 |
| Active | | | | | | | |
| % MCT (Primary C8; Miglyol 808 or NeoBee 895) | 50% | 50% | 50% | 60% | 50% | 50% | 50% |
| Surfactants | | | | | | | |
| % Kolliphor RH40 | 2.50% | 2.50% | 2.50% | 3.00% | 2.50% | 2.50% | 2.50% |
| % Lecithin | 2.50% | 2.50% | 2.50% | 3.00% | 2.50% | 2.50% | 2.50% |
| Co-Surfactants | | | | | | | |
| % Imwitor 308 % Capmul 808G | 5.00% | 5.00% | 5.00% | 6.00% | 5.00% | 5.00% | 5.00% |
| Film-Forming Polymers | | | | | | | |
| % PVP-VA 64 | 20% | 20% | 20% | 14% | 20% | 20% | |
| % Dextran70 | | | | | | | 20% |
| Adsorbent | | | | | | | |
| % Cab-o-sil (M-5P) | 20% (in ethanol) | 20% (in water) | 20% | 14% | | | 20% |
| % Aerosil 300 | | | | | 20% | | |
| % Neusilin UFL2 | | | | | | 20% | |
| % Total | 100% | 100% | 100% | 100% | 100% | 100% | 100% |
| Results | High film forming polymer and high cabosil, in emulsion; moderate spray yield (42%) with well-defined particles | High film forming polymer and high cabosil, in solution; good spray yield (64%) with well-defined particles | Repeat of F-2 with Miglyol 808; moderate yield spray; primary particle size 10-30 μm; moderate agglomeration | Higher active loading; moderate yield spray (49.6%); primary particle size 10-30 μm; heavy agglomeration | Areosil 300; low yield spray; primary particle size 10-30 μm; heavy agglomeration | Neusilin UFL2; low yield spray; primary particle size 10-30 μm; moderate agglomeration | Dextran 70; low yield spray; primary particle size 10-20 μm; no agglomeration, well defined particles |

TABLE 1-1B

| | Exemplary Compositions | | | | | |
|---|---|---|---|---|---|---|
| | F-8 | F-9 | F-10 | F-11 | F-12 | F-13 |
| Active | | | | | | |
| % MCT (Primary C8; Miglyol 808 or NeoBee 895) | 50% | 50% | 50% | 60% | 40% | 50% |
| Surfactants | | | | | | |
| % Kolliphor RH40 | 2.50% | 2.50% | 2.50% | 3.00% | 2.00% | 2.50% |
| % Lecithin | 2.50% | 2.50% | 2.50% | 3.00% | | |
| % Phospholipon 90G | | | | | 2.00% | 2.50% |

TABLE 1-1B-continued

| | \multicolumn{6}{c}{Exemplary Compositions} | | | | | |
|---|---|---|---|---|---|---|
| | F-8 | F-9 | F-10 | F-11 | F-12 | F-13 |
| Co-Surfactants | | | | | | |
| % Imwitor 308 | 5.00% | 5.00% | 5.00% | 6.00% | | |
| % Capmul 808G | | | | | 4.00% | 5.00% |
| Film-Forming Polymers | | | | | | |
| % PVP-VA 64 | 30% | 10% | 10% | 8% | 15% | 10% |
| % Dextran70 | | | 10% | | | |
| Adsorbent | | | | | | |
| % Cab-o-sil (M-5P) | 10% | 30% | 20% | 20% | 37% | 30% |
| % Aerosil 300 | | | | | | |
| % Neusilin UFL2 | | | | | | |
| % Total | 100% | 100% | 100% | 100% | 100% | 100% |
| Results | Increased PVPVA, decreased cabosil; low yield spray | Increased cabosil, decreased PVPVA; good yield (63) and good particle formation | Add Dextran 70 to reduce initial viscosity; low yield | Higher active loading and higher cabosil: PVPVA ratio; high yield (101.5) | 40% API; good spray yields (~90-94%) with well-defined particles | 50% API; moderate yields with well-defined particles |

Figure 2B:
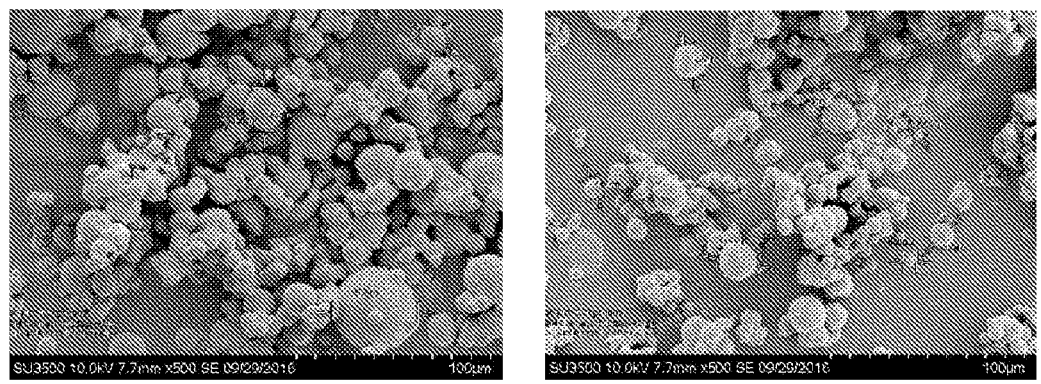
Figure 2C:
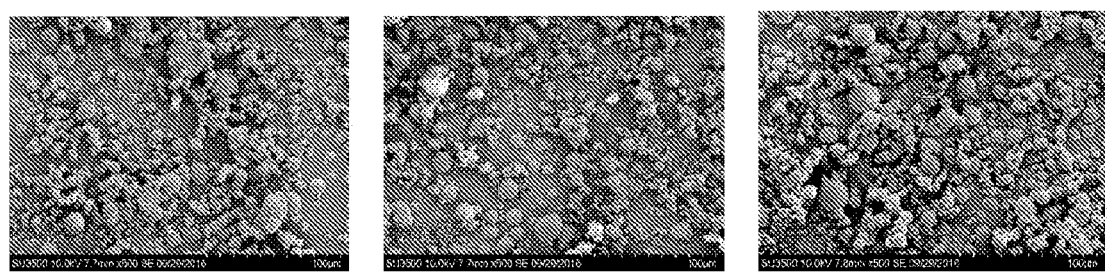

SEM was performed on exemplary compositions, as shown in FIG. 2. Irregular, agglomerated particles observed for all 60% active sprays; discrete particles with some particle fusion observed with 50% active sprays; and discrete particles observed for all 40% active sprays, regardless of processing conditions.

Comparative compositions were prepared in a manner similar to that described herein for the exemplary compositions of the disclosure, as described in Tables 1-2A and 1-2B below.

TABLE 1-2A

| | \multicolumn{6}{c}{Comparative Compositions} | | | | | |
|---|---|---|---|---|---|---|
| | C-1 (SD-23) | C-2 (SD-27) | C-3 (SD-19) | C-4 (SD-20) | C-5 (SD-24) | C-6 (SD-28) |
| Active | | | | | | |
| % MCT (Primary C8; Miglyol 808 or NeoBee MCT895) | 50% | 50% | 50% | 50% | 60% | 50% |
| Surfactants | | | | | | |
| % Kolliphor RH40 | 2.50% | 2.50% | | | | 2.50% |
| % Lecithin | 2.50% | 2.50% | | | | 2.50% |
| Co-Surfactants | | | | | | |
| % Imwitor 308 | 5.00% | 5.00% | | | | 5.00% |
| Bulking Agent | | | | | | |
| % Maltodextrin | 38% | 20% | 24% | | | |
| % Acacia | | | 24% | 48% | | |
| % K + caseinate | | | | | 38% | |
| Film Forming Polymer | | | | | | |
| % PVP-VA 64 | | | | | | 40% |

TABLE 1-2A-continued

Comparative Compositions

| | C-1 (SD-23) | C-2 (SD-27) | C-3 (SD-19) | C-4 (SD-20) | C-5 (SD-24) | C-6 (SD-28) |
|---|---|---|---|---|---|---|
| Adsorbent | | | | | | |
| % Cab-o-sil (M-5P) | 2% | 20% | 2% | 2% | 2% | |
| % Total Results | 100% Oiled out; poor spray | 100% Oiled out; poor spray | 100% Low yield and poor spray with heavy fusion | 100% Low yield and poor spray with heavy fusion | 100% Low yield and poor spray; moderate fusion with larger particle size | 100% All PVPVA, no cabosil; material is waxy and clumped; No discreet, well defined particles |

TABLE 1-2B

Comparative Compositions

| | C-7 (SD-2) | C-8 (SD-4) | C-9 (SD-5) | C-10 (SD-7A) | C-11 (SD-22) |
|---|---|---|---|---|---|
| Active | | | | | |
| % MCT (Primary C8; Miglyol 808 or NeoBee MCT895) | 55% | 55% | 50% | 50% | 50% |
| Surfactants | | | | | |
| % Kolliphor RH40 | 10.3% | 3.75% | 5% | 10.3% | |
| % Lecithin | | 3.75% | 5% | | 5% |
| Co-Surfactants | | | | | |
| % Imwitor 308 | 6.9% | 7.5% | 10% | 6.9% | |
| % Lauroglycol 90 | 2.9% | | | 2.9% | |
| Bulking Agent | | | | | |
| % Maltodextrin | 25% | 30% | | | 21.5% |
| % Acacia | | | 30% | 25% | 21.5% |
| % K + caseinate | | | | | |
| Adsorbent | | | | | |
| % Cab-o-sil (M-5P) | | | | 5% | 2% |
| % Total Results | 100% Waxy solid | 100% Waxy solid | 100% Not sprayed; solution phase separated | 100% Waxy solid; poor yield | Oiled out; no powder collected |

As reflected in the tables above, when comparative examples are prepared using a standard bulking agent with poor film forming properties, the compositions did not provide good spray dried compositions. The spray dried material either oil out or form waxy solids and cannot be efficiently spray dried. Even compositions using adsorbents and desired surfactant ratios do not provide compositions that can be efficiently be spray dried to form discrete particles.

Example 2

Exemplary Preparation of Spray Dried Powder Compositions

Figure 3:
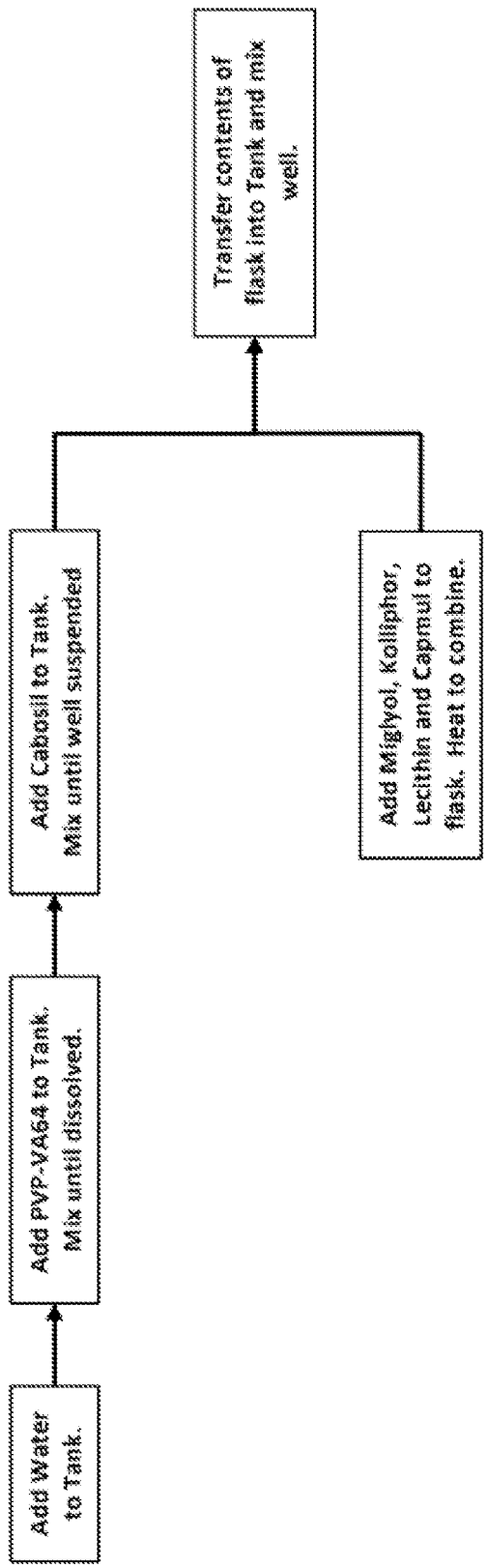
FIG. 3 illustrates an exemplary order of component addition in making pharmaceutical compositions of the disclosure.

Manufacture of the spray dried powder composition of the disclosure may be improved with specified order of component addition. Specifically, it was found that manufacturing processability may be improved if the film forming polymer is dissolved in aqueous solvent prior to the addition of the adsorbent. See FIG. 3 for further description of the order of component addition.

As shown in Table 2-1 below, it was found that if the film forming polymer is added after the adsorbent has been wetted by aqueous solvent, the viscosity of the mix increases and becomes difficult to thereafter spray dry.

TABLE 2-1

| | Composition | | |
|---|---|---|---|
| | F-11 60/3/3/6/8/20 Miglyol 808/Kolliphor RH 40/Phospholipon 90G/Capmul 808G/PVP-VA 64/Cabosil M5P | | |
| | Rationale | | |
| | PVP-VA added after Cabosil wetting (no homogenization) | Cabosil added after PVP-VA (no homogenization) | Cabosil added after PVP-VA (with homogenization) |
| Atomizer (2-Fluid) | 1650-64 (Liquid Cap - Air Cap) | | |
| Atomization Pressure (PSI) | 10 | | |
| Feed Rate (ml/min) | 10 | | |
| Solids Loading (wt %) | 25 | | |
| Inlet Temp (deg C.) | 155 | | |
| Outlet Temp (deg C.) | 65 | | |
| Batch Size (g-solid) | 25 | | |
| Results | Adding Cabosil first causes solution to gel with the addition of PVP-VA; difficult to spray dry | Improved viscosity with no gelling. No difference in yield or particle morphology with or without homogenization | Improved viscosity with no gelling. No difference in yield or particle morphology with or without homogenization |
| Yield (%) | ~50 | 55 | 50 |

Further properties of the spray drying process were investigated, as reflected in Table 2-2 below. In general, it was found that spray outlet temperature did not significantly impact powder properties. However, better yield and better powder properties were observed with higher atomization.

TABLE 2-2

| | Composition | | | | |
|---|---|---|---|---|---|
| | F-13 50/2.5/2.5/5/10/30 Miglyol 808/Kolliphor RH 40/ Phospholipon 90G/Capmul 808G/ PVP-VA 64/Cabosil M5P | | F-12 40/2/2/4/15/37 Miglyol 808/Kolliphor RH 40/ Phospholipon 90G/Capmul 808G/ PVP-VA 64/Cabosil M5P | | |
| | Rationale | | | | |
| | 50% Active; Higher Atomization; Centerline $T_{out}$ | 50% Active; Higher Atomization; Low $T_{out}$ | 40% Active; Higher Atomization; Low $T_{out}$; Low Flowrate | 40% Active; Higher Atomization; Centerline $T_{out}$; Low Flowrate | 40% Active; Higher Atomization; Centerline $T_{out}$; Centerline Flowrate |
| Atomizer (2-Fluid) | 2050-64 (Liquid Cap - Air Cap) | | | | |
| Atomization Pressure (PSI) | 50 | | | | |
| Feed Rate (ml/min) | 10 | 10 | 5 | 5 | 10 |
| Solids Loading (wt %) | 25 | | | | |
| Inlet Temp (deg C.) | 155 | 135 | 100 | 130 | 140 |
| Outlet Temp (deg C.) | 65 | 50 | 50 | 65 | 65 |
| Batch Size (g-solid) | 25 | 25 | 25 | 12.5 | 12.5 |

TABLE 2-2-continued

| Composition | | | | |
|---|---|---|---|---|
| F-13<br>50/2.5/2.5/5/10/30<br>Miglyol 808/Kolliphor RH 40/<br>Phospholipon 90G/Capmul 808G/<br>PVP-VA 64/Cabosil M5P | | | F-12<br>40/2/2/4/15/37<br>Miglyol 808/Kolliphor RH 40/<br>Phospholipon 90G/Capmul 808G/<br>PVP-VA 64/Cabosil M5P | |

| Rationale | | | | |
|---|---|---|---|---|
| 50% Active;<br>Higher<br>Atomization;<br>Centerline $T_{out}$ | 50% Active;<br>Higher<br>Atomization;<br>Low $T_{out}$ | 40% Active;<br>Higher<br>Atomization;<br>Low $T_{out}$;<br>Low Flowrate | 40% Active;<br>Higher<br>Atomization;<br>Centerline $T_{out}$;<br>Low Flowrate | 40% Active;<br>Higher<br>Atomization;<br>Centerline $T_{out}$;<br>Centerline<br>Flowrate |
| Results | | | | |
| Outlet temp did not impact powder properties | | Better yield; better powder properties with higher atomization (faster drying, smaller particles with less agglomeration) | | |
| Yield (%) | | | | |
| 45 | 50 | 90 | 92 | 94 |

Example 3

Emulsions of Spray Dried Powder Compositions

Emulsions of exemplary spray dried powder compositions according to the disclosure are made and characterized for droplet size distribution and pH stability. Lipid mixtures are prepared by mixing components at desired ratios. The lipid mixture is prepared at the desired concentration, diluted with water in 1:100 ratio and shaken 15 seconds until milky white emulsion formed.

Samples were filtered to remove any sediment, and prepared at 0.1g caprylic triglyceride/mL in water. Aliquots were pulled at initial pH (4.6), pH 3.0, pH 2.0 and pH 1.2. Aliquot samples were diluted 1:100 in water for analysis by DLS.

Figure 4A:
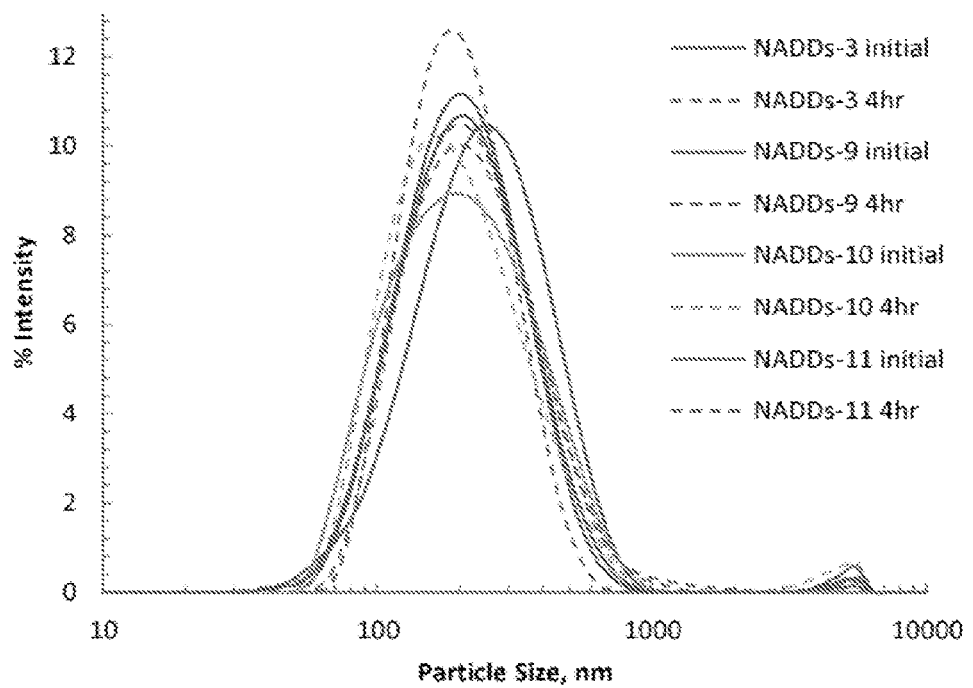
FIG. 4A-4B illustrates particle size distribution of emulsions formed from exemplary compositions of the disclosure (Panel A), as well as particle size distribution and pH stability of emulsions formed from 45% API spray dried compositions (Panel B), in accordance with embodiments of the disclosure.
Figure 4B:
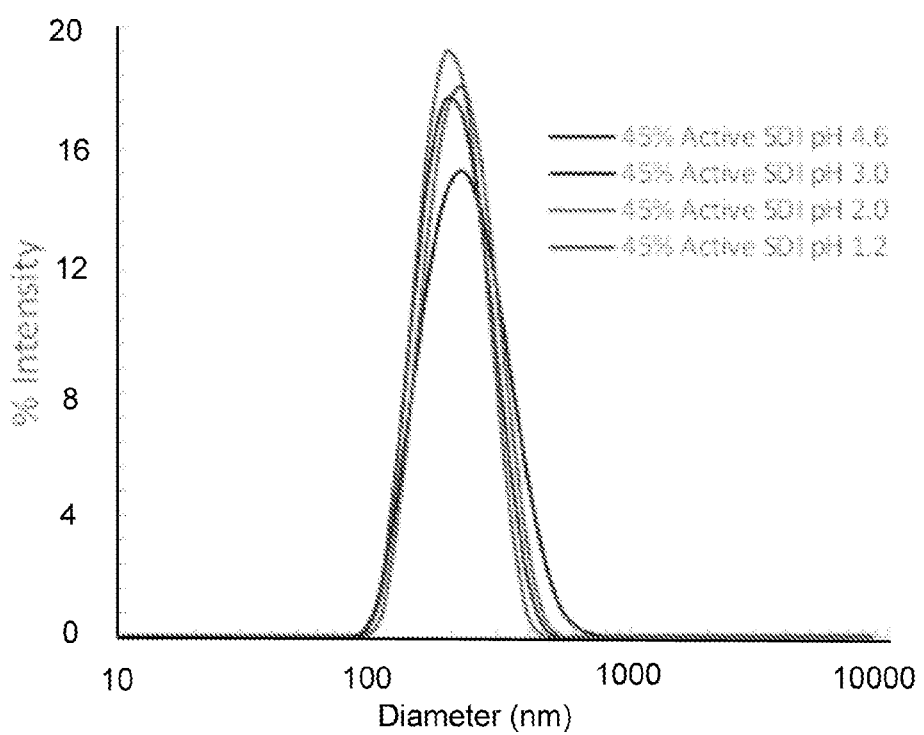

Droplet size of all exemplary compositions tested (F-3, F-9, F-10 and F-11) form similar emulsions with no significant change after 4 hours at ambient conditions (see FIG. 4A) Further, as illustrated in FIG. 4B, 45% API emulsions are stable through pH 1.2, with an emulsion having a mean droplet diameter of between about 200 nm and about 300 nm. After 20 hours, the droplet size decreases slightly, but change is not significant (data not shown).

Example 4

Characterization of Spray Dry Powder Compositions and Emulsions

Three exemplary spray dried compositions of the disclosure were prepared, and the spray dried compositions and resulting emulsions were characterized. The spray dried compositions were characterized by thermal characteristics (DSC), morphology (SEM), particle-size distribution (PSD), water content (KF), bulk/tapped density (BSV/TSV), potency and purity by HPLC-CAD. The re-suspendability of the spray dried compositions was characterized at 0 hr and 4 hr by visual, and DLS analysis and recovery of API (caprylic triglyceride) in the resulting emulsions was determined by HPLC-CAD. In addition, the spray-emulsion was evaluated by DLS and light microcopy and the individual raw excipients were evaluated by HPLC-CAD.

Three compositions were manufactured to evaluate the impact of active loading on yield, as well as particle morphology and quality. Table 4-1 shows the manufacturing summary of the spray drying runs. Runs were conducted in order of increasing active loading. All other processing parameters aside from composition were held constant between the three sprays. Comparable yields were obtained for the 40% and 45% API compositions, however, a decrease in yield was observed for the 50% API composition. Due to the low yield with the 50% API composition, only the 40% and 45% active compositions were further characterized.

TABLE 4-1

| Manufacturing Summary of Spray Dried Compositions | | | |
|---|---|---|---|
| | Lot Number | | |
| | BREC-1678-034 | BREC-1678-054 | BREC1678-074 |
| | Formulation | | |
| | 40/2/4/2/15/37<br>AC-1204/Kolliphor RH40/<br>Capmul 808/Phospholipon 90G/<br>PVP-VA64/Cab-o-Sil | 45/2.25/4.5/2.25/13/33<br>AC-1204/Kolliphor RH40/<br>Capmul 808/Phospholipon 90G/<br>PVP-VA64/Cab-o-Sil | 50/2.5/5/2.5/10/30<br>AC-1204/Kolliphor RH40/<br>Capmul 808/Phospholipon 90G/<br>PVP-VA64/Cab-o-Sil |
| | Formulation constants- 20/1/2/1AC-1204/Kolliphor RH40/Capmul 808/Phospholipon 90G | | |
| Atomizer (2-Fluid) | 2850-120(Liquid Can - Air Cap) | | |
| Atomization Pressure [PSI] | 50 | | |
| Feed Rate [g/min] | 40 | | |
| Solids Loading [wt %] | 25 | | |
| Inlet Temperature [° C.] | 135 | | |

TABLE 4-1-continued

Manufacturing Summary of Spray Dried Compositions

| | Lot Number | | |
|---|---|---|---|
| | BREC-1678-034 | BREC-1678-054 | BREC1678-074 |
| | | Formulation | |
| | 40/2/4/2/15/37 AC-1204/Kolliphor RH40/ Capmul 808/Phospholipon 90G/ PVP-VA64/Cab-o-Sil | 45/2.25/4.5/2.25/13/33 AC-1204/Kolliphor RH40/ Capmul 808/Phospholipon 90G/ PVP-VA64/Cab-o-Sil | 50/2.5/5/2.5/10/30 AC-1204/Kolliphor RH40/ Capmul 808/Phospholipon 90G/ PVP-VA64/Cab-o-Sil |
| | Formulation constants- 20/1/2/1AC-1204/Kolliphor RH40/Capmul 808/Phospholipon 90G | | |
| Outlet Temperature [° C.] | | 65 | |
| ~Batch Size [g-solids] | 2050 | 635 | 330 |
| Yield [%] | 36 | 83 | 56 |

Characterization of 40% and 45% API compositions shows that both compositions exhibit similar characteristics for all analytical tests completed at T0/initial. Qualitative assessment of both compositions by the "squeeze test"— where the spray dried composition is gently squeezed between gloved fingers- showed that the 45% composition appeared slightly more "waxy" compared to the 40% composition, which remained dry and solid. Abbreviated analytical testing of 2-week stability samples shows no significant change from initial for samples stored at any condition, including the harshest condition of 40° C./75% RH.

DSC thermal analysis of 40% and 45% API compositions is shown in FIG. 5, which indicates the two compositions are very similar. Table 4-2 shows a summary of the thermal events for both compositions, and confirms they are very similar in temperature for congealing, and for melt. The enthalpies are slightly higher for the 45% API composition, compared to the 40% API composition.

TABLE 4-2

Tabulated DSC data of 40% and 45% API Spray Dried Compositions

| | Congeal (Cool ramp) | | | Exotherm 2 (Heat ramp) | | | Melt (Heat ramp) | | |
|---|---|---|---|---|---|---|---|---|---|
| Formulation | onset, ° C. | max, ° C. | enthalpy, J/g | onset, ° C. | max, ° C. | enthalpy, J/g | onset, ° C. | max, ° C. | enthalpy, J/g |
| 40% SDI BREC1678-034 | −28.4 ± 0.1 | −31.7 ± −0.1 | 24.2 ± 0.5 | −23.2 ± 0.1 | −18.8 ± 0.2 | 12.3 ± 0.3 | −0.1 ± 0.3 | 5.1 ± 0.7 | 42.3 ± 0.3 |
| 45% SDI BREC1678-054 | −27.9 ± 0.1 | −31.2 ± 0 | 28.2 ± 0.2 | −20.6 ± 0.2 | −15.8 ± 0.3 | 13.1 ± 0.3 | 0.4 ± 0.3 | 5.5 ± 0.8 | 47.1 ± 0.7 |

FIGS. 6A-6B show initial morphology by SEM and indicates mostly discrete spherical particles, with some mild clumping for both 40% (Panel A) and 45% (Panel B) API compositions. Abbreviated analytical testing of 2-week stability samples shows no significant change from initial for samples stored at any condition, including 40° C./75% RH (data not shown).

Figure 7:
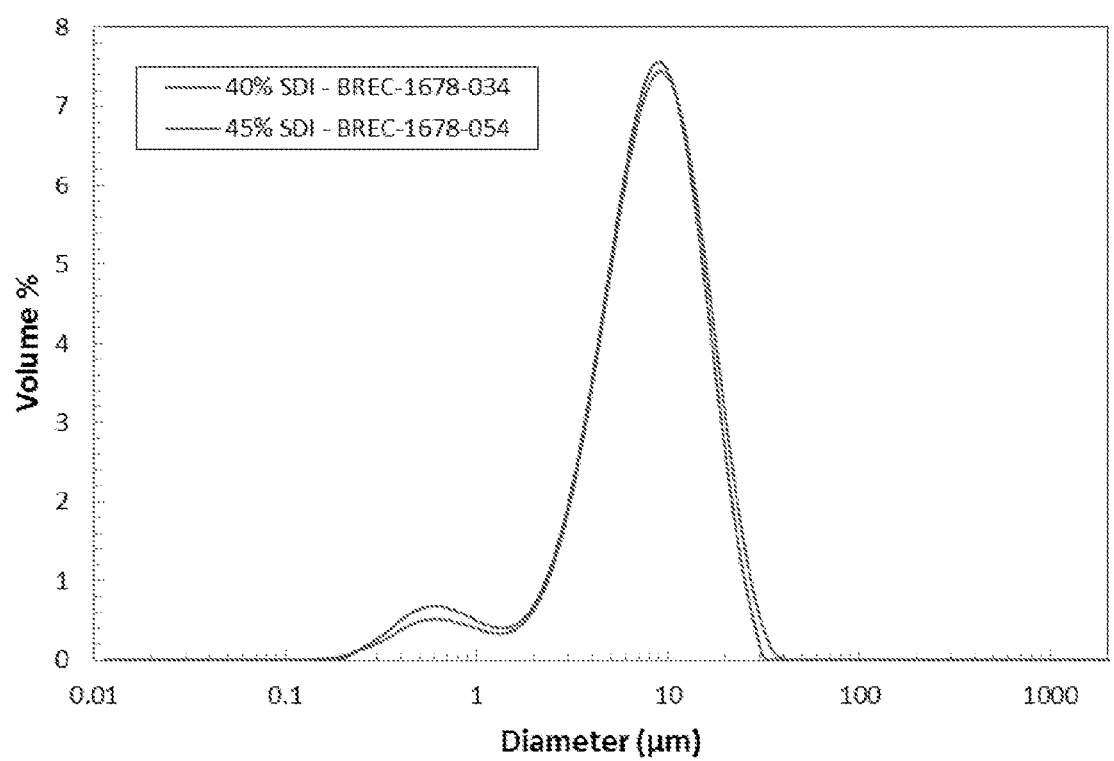
FIG. 7. Illustrates particle size distribution of 40% and 45% API spray dried composition particles by Malvern laser diffraction, in accordance with embodiments of the disclosure.

FIG. 7 shows the particle size distribution is very similar for both 40% and 45% API compositions, and that the particles are very small and in the range between about 1 and 30 µm. Table 4-3 shows the particle size, specifically the D50 is approximately 8 µm, and the span is 1.76-1.77 µm.

TABLE 4-3

Particle size distribution summary of 40% and 45% API Spray Dried Composition particles by Malvern laser diffraction

| Test Ref: BREC-1678-094 | | Averages | | | | | |
|---|---|---|---|---|---|---|---|
| Sample Name | Lot | D(v 0.1) µm | D(v 0.5) µm | D(v 0.9) µm | D[3.2] µm | D[4.3] µm | Span |
| 40% AC-1204 | BREC-1678-034 | 3 | 8 | 16 | 4 | 9 | 1.759 |
| 45% AC-1204 | BREC-1678-054 | 2 | 7 | 15 | 3 | 8 | 1.775 |

BSV/TSV (bulk and tapped density) analysis of both compositions is summarized in Table 4-4. The lower Carr index for 45% API, indicates it may show slightly improved flow compared to the 40% API.

TABLE 4-4

Bulk and Tapped Density of 40% (BREC-1678-034) and
45% (BREC-1678-054) API Spray Dried Compositions

| Lot # | | Bulk Density (g/mL) | Tapped Density (g/mL) | Bulk Specific Volume (mL/g) | Tapped Specific Volume (mL/g) | Carr Index (%) | Hausner Ratio |
|---|---|---|---|---|---|---|---|
| BREC-1678-034 | Min-Max | 0.322-0.325 | 0.484-0.5 | 3.07-3.1 | 2-2.06 | 32.8-35.6 | 1.489-1.553 |
| | Mean | 0.32 | 0.49 | 3.1 | 2.0 | 34 | 1.52 |
| BREC-1678-054 | Min-Max | 0.284-0.29 | 0.341-0.342 | 3.44-3.52 | 2.92-2.93 | 14.8-16.9 | 1.174-1.204 |
| | Mean | 0.29 | 0.34 | 3.5 | 2.9 | 16 | 1.19 |

Water content is shown in Table 4-5, and indicates that both compositions are very similar and have very low water content.

TABLE 4-5

Water content by KF-Oven of 40% and
45% API Spray Dried Compositions

| Sample | Lot | Water Content (%) | Standard Deviation (n = 3) |
|---|---|---|---|
| 40% API | BREC1678-034 | 0.47 | 0.01 |
| 45% API | BREC1678-054 | 0.58 | 0.01 |

Figure 8:
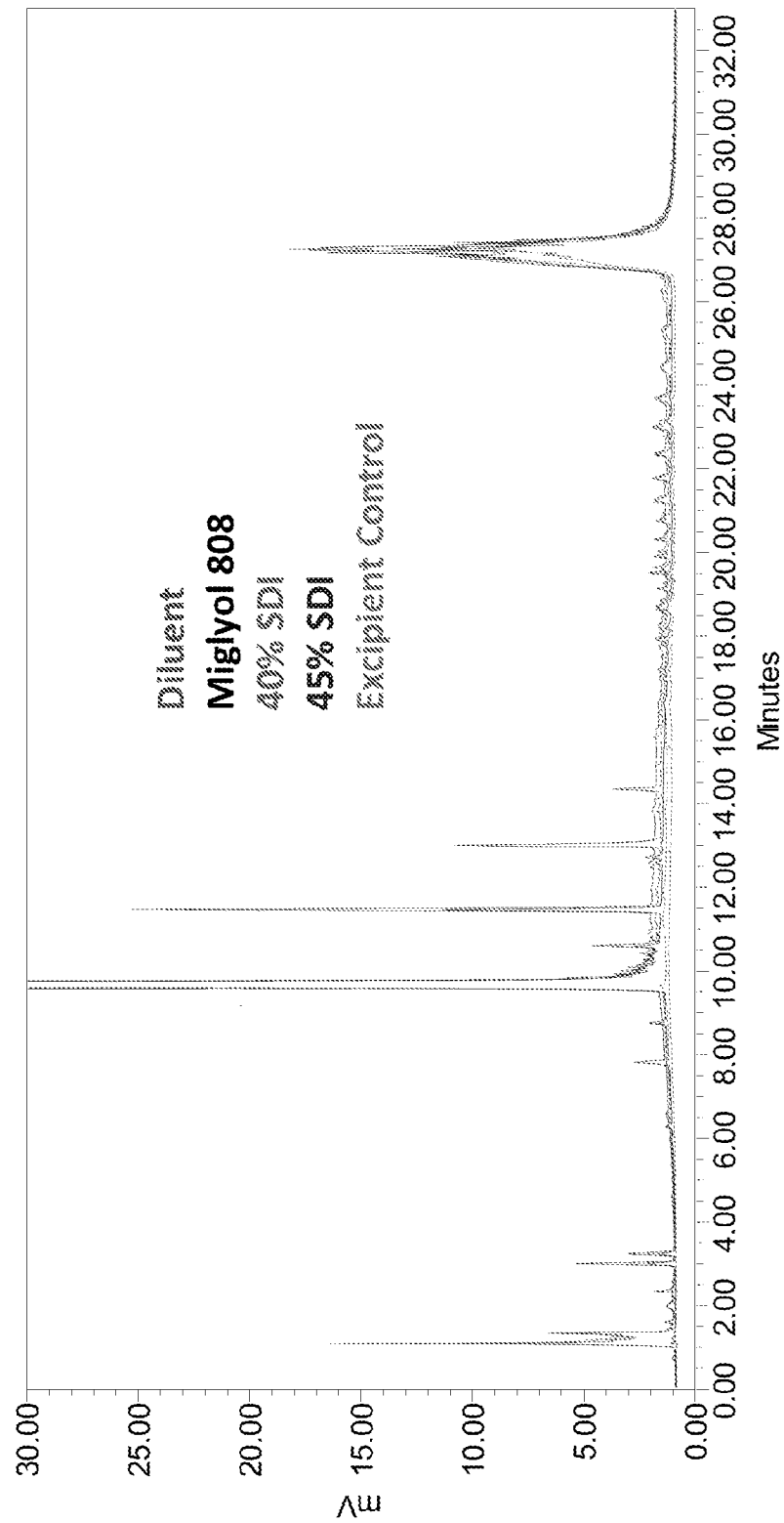
FIG. 8 illustrates representative Chromatograms of Assay/Purity Samples, in accordance with embodiments of the disclosure.

Assay and purity for the 40% and 45% API spray dried compositions are summarized and compared to control Miglyol 808 oil samples. Table 4-6 shows that Caprylic triglyceride potency is approximately 96%-99% and similar for the control compositions (oil control, AC-1204) and both exemplary compositions. The primary impurities C6:C8:C8 are similar for all compositions, at approximately 0.17% average, although the level was significantly lower for the oil. The C10:C8:C8 impurity is approximately 2.15% for all compositions and approximately 0.9% for the oil. The total impurities is approximately 4% for the compositions, and 1.3% for the oil. A representative chromatogram overlay is shown in FIG. 8.

TABLE 4-6

Assay and Purity of 40% and 45% API Spray Dried Compositions

| RRT | Peak ID | Miglyol 808, % | AC-1204 (API), % | 40% SDI, % | 45% SDI, % |
|---|---|---|---|---|---|
| 0.24 | | ND | 0.09% | ND | 0.06% |
| 0.28 | | ND | 0.08% | ND | ND |
| 0.31* | | 0.13% | 0.21% | 0.15% | 0.16% |
| 0.34* | | 0.08% | 0.13% | 0.07% | 0.08% |
| 0.81 | C6:C8:C8 | <LOQ | 0.21% | 0.16% | 0.16% |
| 0.91 | | <LOQ | 0.12% | 0.07% | 0.08% |
| 1.00 | Caprylic Triglyceride | 98.71% | 95.32% | 96.04% | 95.98% |
| 1.10 | | 0.12% | 0.29% | 0.26% | 0.25% |
| 1.19 | C10:C8:C8 | 0.90% | 2.29% | 2.14% | 2.15% |
| 1.30 | | <LOQ | 0.08% | ND | <LOQ |
| 1.32 | | 0.06% | 0.09% | 0.05% | 0.05% |
| 1.35 | | ND | 0.97% | 0.90% | 0.91% |
| 1.48 | | ND | 0.22% | 0.18% | 0.18% |
| 1.61 | | ND | ND | <LOQ | ND |
| — | Total Impurities | 1.29% | 4.68% | 3.96% | 4.02% |
| — | Assay (% LC) | — | — | 100.8% ± 0.1% | 101.1% ± 1% |

LOQ > 0.05%
*RRT 0.31 & 0.34 were corrected for contribution from Capmul 808G

Figure 9:
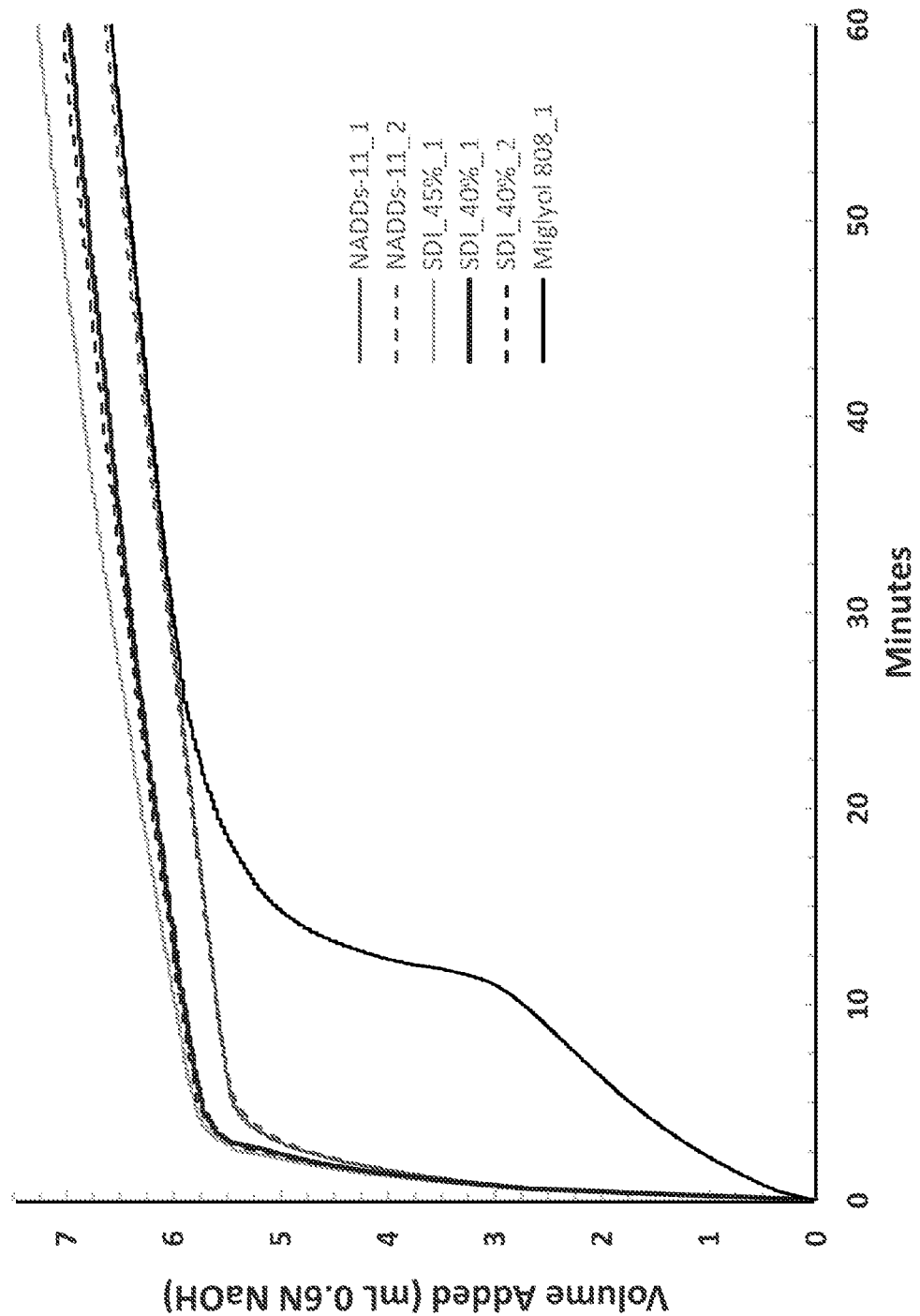
FIG. 9 illustrates digestion pH titration curves for 40% and 45% API spray dried compositions, F-11 (NADDs-11), and Miglyol 808 oil, in accordance with embodiments of the disclosure.

The digestion pH titration curves for both compositions, as well as control samples F-11 and the Miglyol 808 oil are shown in FIG. 9. All spray dried compositions have immediate and complete digestion, while the Miglyol 808 oil has a sigmoidal titration curve, and is slower to reach the endpoint.

Figure 10:
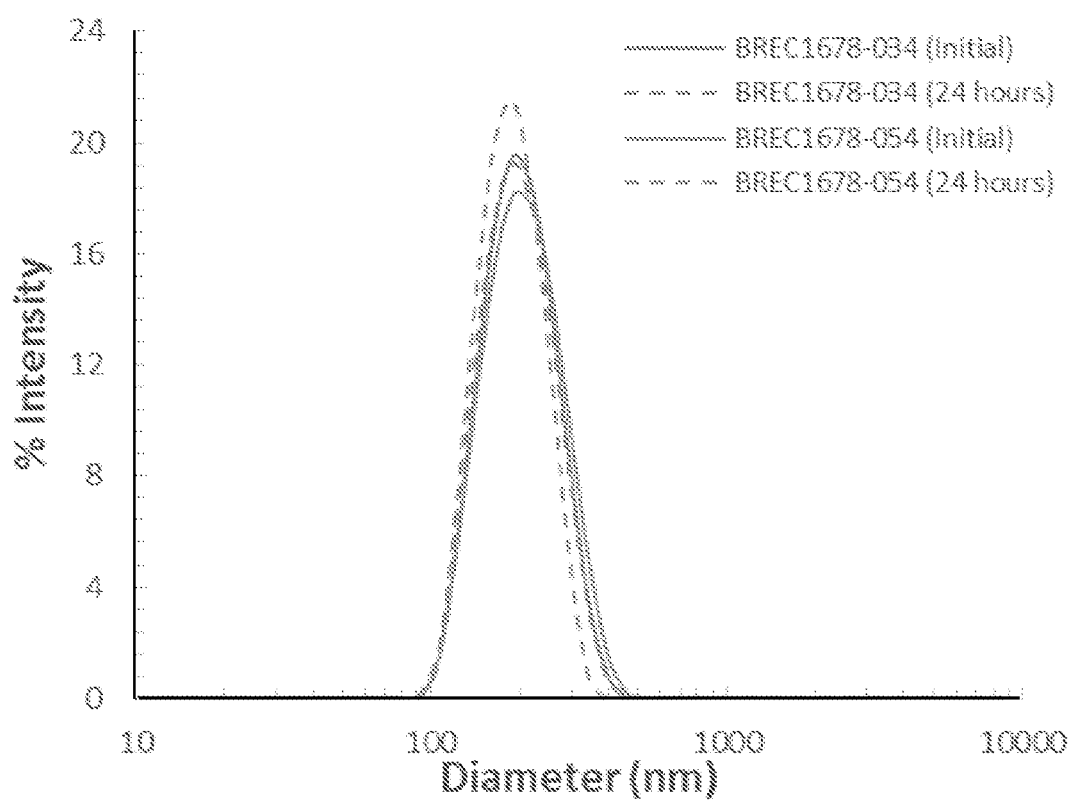
FIG. 10 illustrates droplet size distribution of emulsions formed from 40% and 45% API spray dried compositions @ 0.1gA/mL, in accordance with embodiments of the disclosure.
Figure 11A:
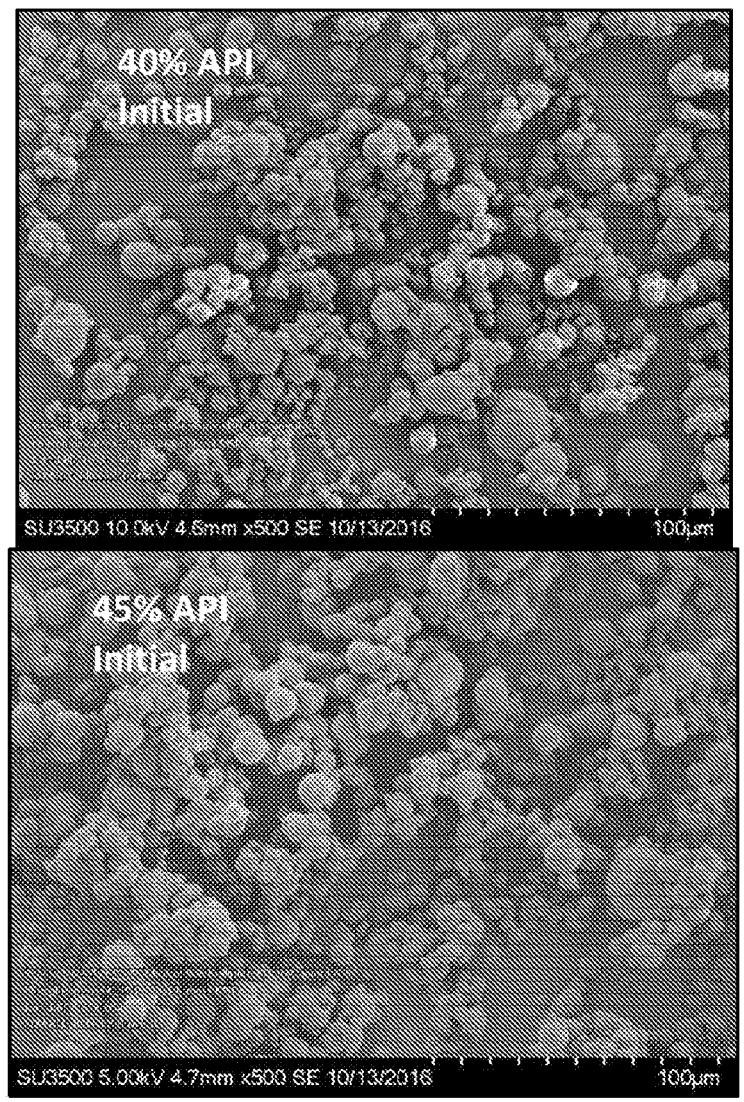
FIGS. 11A-11D illustrate SEM images of 40% and 45% API spray dried composition particles at 500× magnification (Panel A, initial; Panel B, after 2 weeks at 5° C.; Panel C, after 2 weeks at 25° C./60% RH; Panel D, after 2 weeks at 40° C./75% RH), in accordance with embodiments of the disclosure.
Figure 11B:
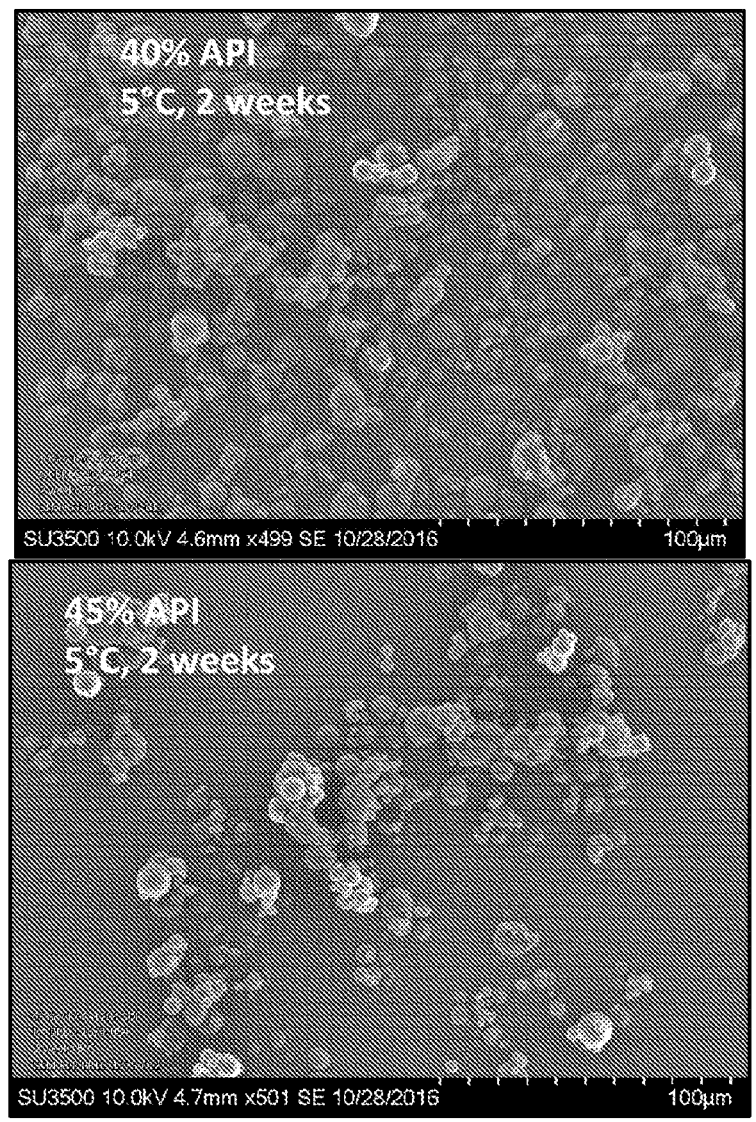
Figure 11C:
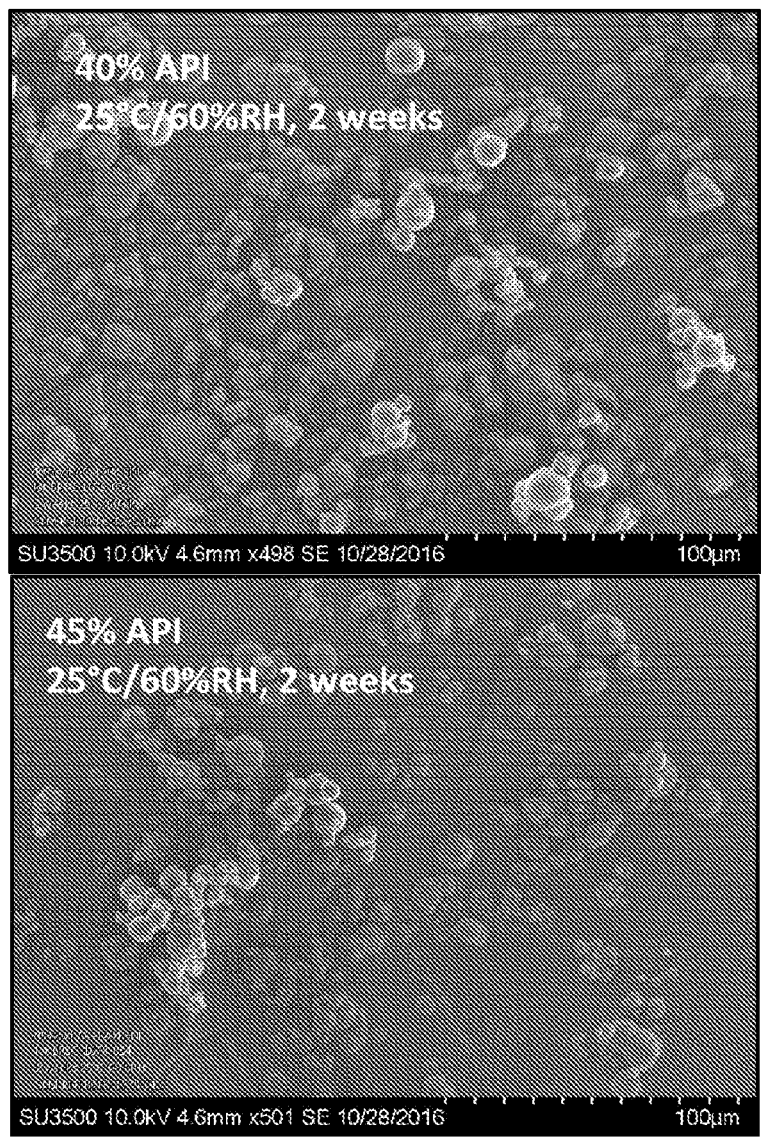
Figure 11D:
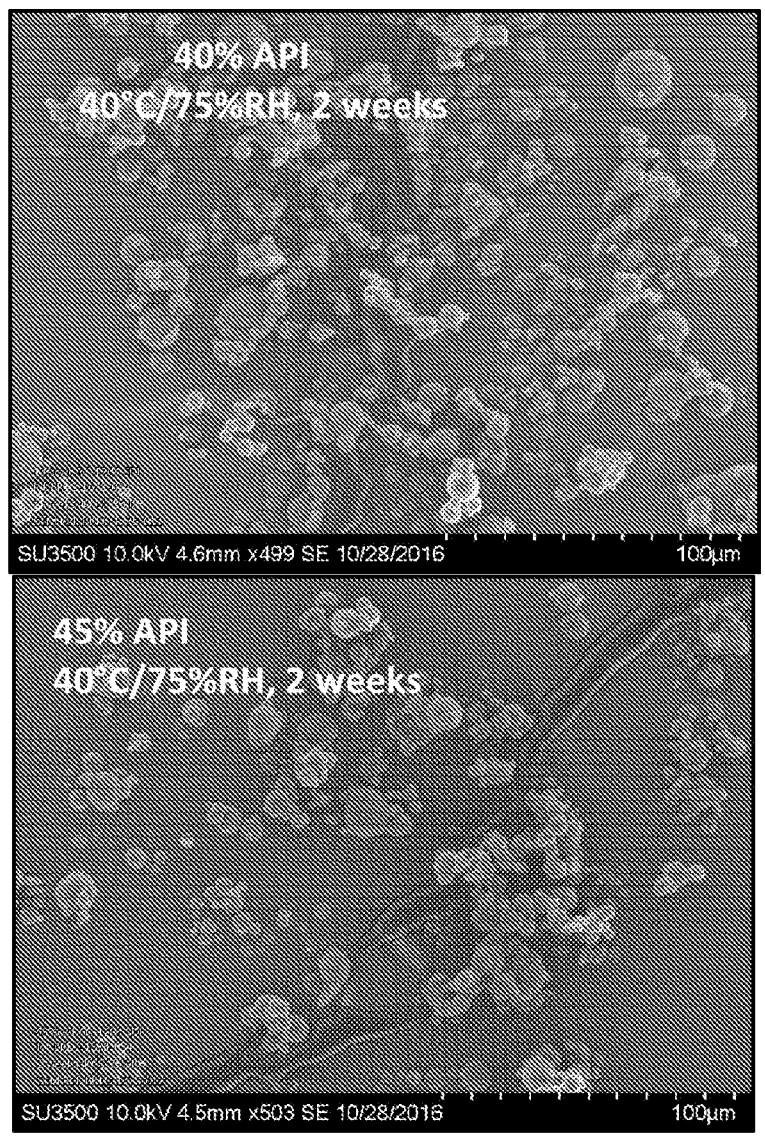
Figure 13A:
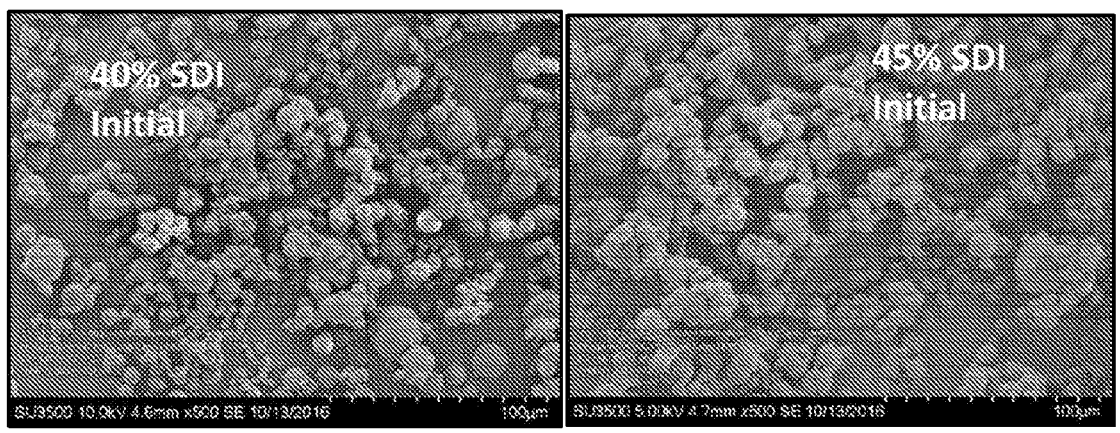
FIGS. 13A-13D illustrate SEM Images of 40% and 45% API spray dried composition particles at 500× magnification (Panel A, initial; Panel B, after 1 month at 5° C.; Panel C, after 1 month at 25° C./60% RH; Panel D, after 1 month at 40° C./75% RH), in accordance with embodiments of the disclosure.
Figure 13B:
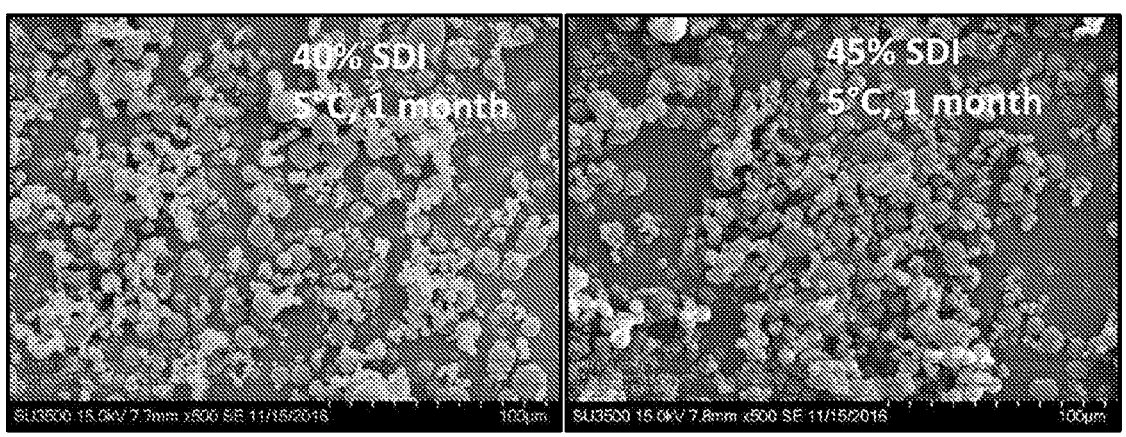
Figure 13C:
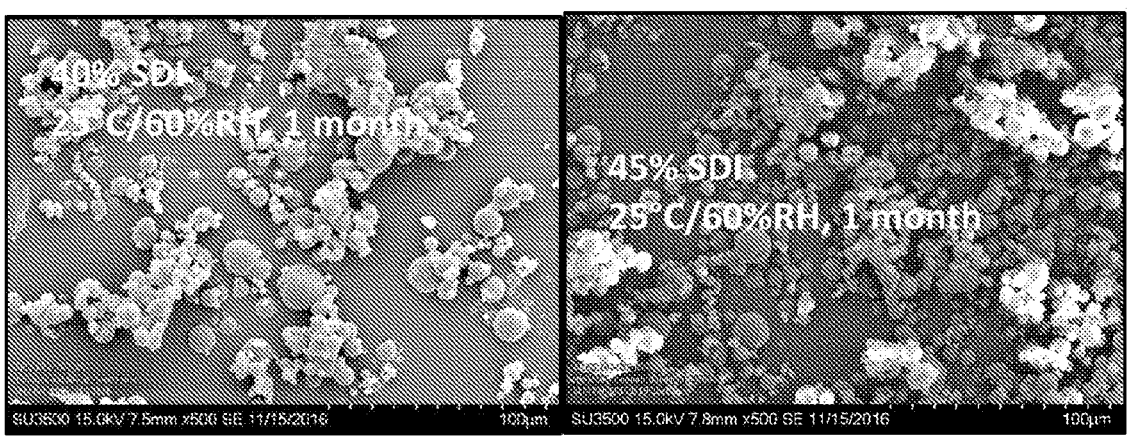
Figure 13D:
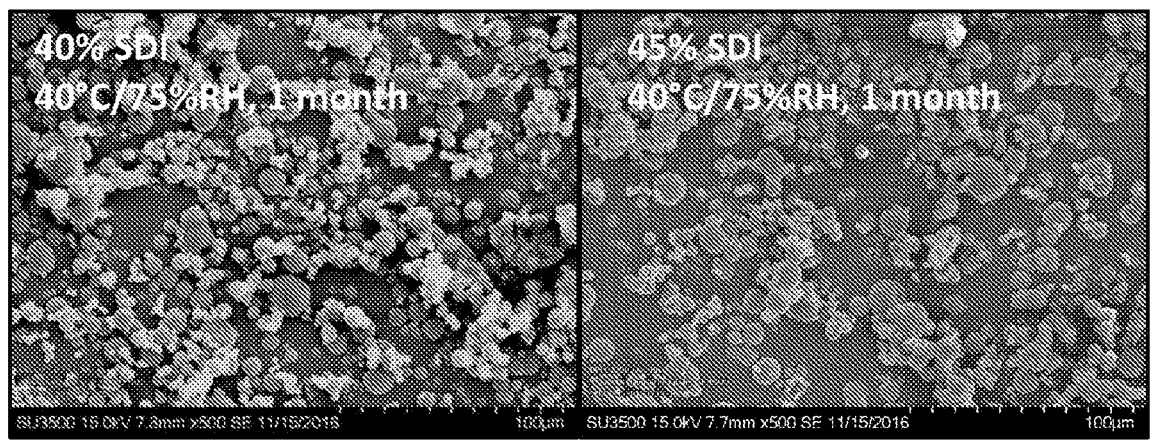

The emulsion droplet size of both compositions at initial and after 24 hrs at ambient conditions is shown in FIG. 10. Both compositions have similar droplet size and neither changes size significantly after 24 hrs, as shown in summary in Table 4-7.

TABLE 4-7

Droplet Size Distribution of Emulsion formed from 40% and
45% API Spray Dried Compositions @ 0.1 gA/mL

| Sample | Lot | Z-Average (nm) | PdI |
|---|---|---|---|
| 40% SDi at 0.1 gA/mL in water (intial) | BREC1678-034 | 192 | 0.05 |
| 40% SDi at 0.1 gA/mL in water (24 hours) | BREC1678-034 | 188 | 0.07 |
| 45% SDi at 0.1 gA/mL in water (intial) | BREC1678-054 | 196 | 0.07 |
| 45% SDi at 0.1 gA/mL in water (24 hours) | BREC1678-054 | 182 | 0.04 |

Recovery of API (caprylic triglyceride) from the emulsion was measured by assaying the emulsion. The recovery from both compositions is similar and approximately 76-79% of theoretical, as shown in Table 4-8.

TABLE 4-8

Recovery of API from Emulsion for 40%
and 45% API Spray Dried Compositions

| Sample | Lot | Recovery of Caprylic Triglyceride (% Theoretical) | Range (n = 2) |
|---|---|---|---|
| 40% API | BREC1678-034 | 79.5 | 6.6 |
| 45% API | BREC1678-054 | 76.3 | |

Example 5

Stability of Spray Dried Compositions and Emulsions

Approximately 4 gm of spray dried composition powder produced according to Example 4 was weighed into PE bags and placed inside heat-sealed foil pouches without desiccant. Samples were loaded into appropriate stability chamber, and time points and conditions are shown in Table 5-1. Analytical testing to include appearance, SEM morphology, Malvern PSD, water content, DSC thermal analysis, assay and purity, and re-suspendability of emulsion by DLS.

TABLE 5-1

Stability protocol for 40% and 45% API Spray Dried Compositions

| Sample and Lot | Time Point | Condition |
|---|---|---|
| 40% API, lot BREC 1678-034 | Initial - T0 | N/A |
| 45% API, lot BREC 1678-054 | | |
| 40% API, lot BREC 1678-034 | 2 weeks | 5° C. |
| 45% API, lot BREC 1678-054 | | 25° C./60% RH |
| | | 40° C./75% RH |
| 40% API, lot BREC 1678-034 | 1 month | 5° C. |
| 45% API, lot BREC 1678-054 | | 25° C./60% RH |
| | | 40° C./75% RH |

Test Results at 2 Weeks

Analytical testing of 2-week stability samples shows no significant change from initial for samples stored at any condition, including 40° C./75% RH. Composition particle morphology of 40% and 45% API compositions is shown in FIGS. 11A-11D, Panel A showing initial time point, Panel B showing 5° C.; Panel C showing 25° C./60% RH; and Panel D showing 40° C./75% RH. Morphology has not significantly changed for 40% and 45% API compositions at 2-weeks and any condition.

Particle size distribution is very similar to initial for 40% (Panel A) and 45% (Panel B) API compositions at 2-weeks and any condition (data table provided in Panel C), as shown in FIGS. 12A-12C.

At two weeks, the initial droplet size of the emulsion formed is larger than observed for the initial powders. After 24 hours, the emulsion droplet size has reduced to the same range as initial. The effect was more pronounced for the 40% API composition and the magnitude of the shift trends with increasing stability condition. Table 5-2 summarizes the emulsion droplet size and stability up to 24 hrs for the 40% API composition, and Table 5-3 summarizes the emulsion droplet size and stability up to 24 hrs for the 45% API composition.

TABLE 5-2

Emulsion droplet size data for 40% API Spray Dried Compositions stored for 2 weeks on stability verses initial

| Condition | Timepoint | Z-Average (nm) | PDL |
|---|---|---|---|
| 5° C. | T = 0 (initial) | 192 | 0.05 |
| | 2 week (initial) | 228 | 0.17 |
| | T = 0 (24 hour) | 188 | 0.07 |
| | 2 week (24 hour) | 185 | 0.04 |
| 25° C./60% RH | T = 0 (initial) | 192 | 0.05 |
| | 2 week (initial) | 272 | 0.23 |
| | T = 0 (24 hour) | 188 | 0.07 |
| | 2 week (24 hour) | 194 | 0.05 |
| 40° C./75% RH | T = 0 (initial) | 192 | 0.05 |
| | 2 week (initial) | 284 | 0.20 |
| | T = 0 (24 hour) | 188 | 0.07 |
| | 2 week (24 hour) | 194 | 0.08 |

40% SDI at 0.1 gA/mL in water

TABLE 5-3

Emulsion droplet size data for 45% API Spray Dried Compositions stored for 2 weeks on stability verses initial

| Condition | Timepoint | Z-Average (nm) | PDL |
|---|---|---|---|
| 5° C. | T = 0 (initial) | 196 | 0.07 |
| | 2 week (initial) | 223 | 0.12 |
| | T = 0 (24 hour) | 182 | 0.04 |
| | 2 week (24 hour) | 189 | 0.03 |
| 25° C./60% RH | T = 0 (initial) | 196 | 0.07 |
| | 2 week (initial) | 233 | 0.15 |
| | T = 0 (24 hour) | 182 | 0.04 |
| | 2 week (24 hour) | 194 | 0.04 |
| 40° C./75% RH | T = 0 (initial) | 196 | 0.07 |
| | 2 week (initial) | 229 | 0.13 |
| | T = 0 (24 hour) | 182 | 0.04 |
| | 2 week (24 hour) | 192 | 0.05 |

45% SDI at 0.1 gA/mL in water

Water content is summarized in Table 5-4, and is very low for all composition samples and all conditions at 2-weeks. Water content for 40% API samples at all conditions at 2-weeks is slightly higher than initial, but still very dry. Water content for 45% API samples at 5° C. and 25° C./60% RH conditions at 2-weeks is similar to initial, 45% API stored at 40° C./75% RH for 2-weeks is slightly higher than initial.

TABLE 5-4

Water content of samples on stability verses initial values

| Sample | Condition | % Water |
|---|---|---|
| 40% AC-1204 SDI Lot: BREC1678-034 | Initial | 0.47 ± 0.01 |
| | 2 wk @ 5° C. | 0.70 ± 0.01 |
| | 2 wk @ 25° C./60% RH | 0.71 ± 0.01 |
| | 2 wk @ 40° C./75% RH | 0.69 ± 0.00 |
| 45% AC-1204 SDI Lot: BREC1678-054 | Initial | 0.58 ± 0.01 |
| | 2 wk @ 5° C. | 0.63 ± 0.01 |
| | 2 wk @ 25° C./60% RH | 0.63 ± 0.01 |
| | 2 wk @ 40° C./75% RH | 0.72 ± 0.02 |

DSC thermal events demonstrate that both 40% and 45% API compositions at all conditions for 2-weeks are very similar (data not shown). The congealing temperature upon cooling is approximately −31° C. for both compositions at all conditions, but enthalpy is slightly higher for the 45% API composition, compared to the 40% API composition. Exotherm 2 and Melt temperature upon heating is very similar for all samples, and again—the enthalpies are slightly larger for the 45% API composition, compared to the 40% API composition.

Assay and purity measured for 40% API composition stored 2 weeks is summarized and compared to initial in Table 5-5, and for 45% API composition stored 2 weeks is summarized and compared to initial in Table 5-6. Assay for both compositions stored 2-weeks and at all conditions is similar to initial and in the range of 100% LC to 106% LC. No significant difference in total impurities was observed for either 40% or 45% API compositions at any condition compared to initial, although there was a slight increase that trends with increasing storage condition/temperature. The total impurities for the 40% API composition at 2-weeks is approximately 4.4%, and slightly trends upward with condition/temperature. The total impurities for the 45% API composition at 2-weeks is approximately 4.5%, and slightly trends upward with condition/temperature as well.

TABLE 5-5

Assay and Purity for 40% API Spray Dried Compositions stored 2-weeks

| RRT | Peak ID | 40% SDI, Initial | 40% SDI, 5 C. | 40% SDI, 25 C./ 60% RH | 40% SDI, 40 C./ 75% RH |
|---|---|---|---|---|---|
| 0.24 | | ND | ND | ND | ND |
| 0.31* | | 0.15% | 0.19% | 0.20% | 0.20% |
| 0.34* | | 0.07% | 0.11% | 0.12% | 0.11% |
| 0.81 | C6:C8:C8 | 0.16% | 0.20% | 0.20% | 0.20% |
| 0.91 | | 0.07% | 0.12% | 0.12% | 0.12% |
| 1.00 | Caprylic Triglyceride | 96.04% | 95.57% | 95.51% | 95.37% |
| 1.10 | | 0.26% | 0.29% | 0.29% | 0.31% |
| 1.19 | C10:C8:C8 | 2.14% | 2.21% | 2.30% | 2.29% |
| 1.30 | | ND | 0.07% | 0.07% | 0.07% |
| 1.32 | | 0.05% | 0.09% | 0.08% | 0.09% |
| 1.35 | | 0.90% | 0.97% | 1.02% | 1.03% |
| 1.48 | | 0.18% | 0.23% | 0.23% | 0.24% |
| 1.61 | | <LOQ | ND | ND | ND |
| — | Total Impurities | 3.96% | 4.43% | 4.49% | 4.63% |
| — | Assay | 100.8% ± 0.1% | 103.8% ± 1.8% | 105.7% ± 0.1% | 101.2% ± 5.3% |

ND = not detected,
LOQ > 0.05%,
LOD > 0.02%
*RRT 0.31 & 0.34 were corrected for contribution from Capmul 808G

TABLE 5-6

Assay and Purity for 45% API Spray Dried Compositions stored 2-weeks

| RRT | Peak ID | 45% SDI, Initial | 45% SDI, 5 C. | 45% SDI, 25 C./ 60% RH | 45% SDI, 40 C./ 75% RH |
|---|---|---|---|---|---|
| 0.24 | | 0.06% | ND | ND | ND |
| 0.31* | | 0.16% | 0.20% | 0.20% | 0.22% |
| 0.34* | | 0.08% | 0.11% | 0.11% | 0.12% |
| 0.81 | C6:C8:C8 | 0.16% | 0.20% | 0.21% | 0.21% |
| 0.91 | | 0.08% | 0.11% | 0.12% | 0.12% |
| 1.00 | Caprylic Triglyceride | 95.98% | 95.48% | 95.36% | 95.29% |
| 1.10 | | 0.25% | 0.30% | 0.30% | 0.30% |
| 1.19 | C10:C8:C8 | 2.15% | 2.28% | 2.30% | 2.32% |
| 1.30 | | <LOQ | 0.08% | 0.07% | 0.07% |
| 1.32 | | 0.05% | ND | 0.08% | 0.08% |
| 1.35 | | 0.91% | 1.00% | 1.01% | 1.03% |
| 1.48 | | 0.18% | 0.24% | 0.23% | 0.24% |
| 1.61 | | ND | ND | ND | ND |
| — | Total Impurities | 4.02% | 4.52% | 4.64% | 4.71% |
| — | Assay | 101.1% ± 1% | 102.1% ± 2.9% | 102.4% ± 1.2% | 105.5% ± 1.1% |

ND = not detected,
LOQ > 0.05%,
LOD > 0.02%
*RRT 0.31 & 0.34 were corrected for contribution from Capmul 808G Test Results at 1 Month Spray dried powder particle morphology of 40% and 45% API compositions is shown in FIGS. 13A-13D, Panel A showing initial time point, Panel B showing 5° C.; Panel C showing 25° C./60% RH; and Panel D showing 40° C./75% RH. Morphology has not significantly changed for 40% and 45% API compositions at 1-month for any condition. The appearance of the composition powders after storage for 1 month on stability are unchanged for the initial observations. The powders are white to off-white free flowing powder with little to no clumping (data not shown).

Particle size distribution is very similar to initial for 40% (Panel A) and 45% (Panel B) API compositions at 1 month and any condition (data table shown in Panel C), as shown in FIGS. 14A-14C.

There is a reproducible increase in droplet size for T=0 emulsions formed from the aged compositions. 24 hours after the emulsion is formed the droplet size decreased to values very similar to the initial compositions. The equilibrium droplet size is approximately 190nm for all samples. As Table 5-7 and FIGS. 15A-15D show, no significant difference in emulsion droplet size is observed as a function of stability storage condition or age for the 24 hour emulsions. FIGS. 15A-15D illustrates droplet size distribution for emulsions formed from 40% (Panel A, initial; Panel B, after 4 to 24 hours) and 45% (Panel C, initial; Panel D, after 4 to 24 hours) API spray dried compositions. The second set of droplet measurements was performed after 4 hrs, rather than 24 hrs.

TABLE 5-7

Emulsion droplet size of composition samples on stability after 1 month compared to initial and 2-week timepoints

| Condition | Timepoint | Z-Average (nm) | PdI |
|---|---|---|---|
| 40% SDI lot: BREC1678-034 | | | |
| Initial | Initial (t = 0, t = 24 hr) | 192, 188 | 0.055, 0.069 |
| 5° C. | 2 week (t = 0, t = 24 hr) | 228, 185 | 0.172, 0.039 |
| | 1 month (t = 0, t = 4 hr) | 237, 182 | 0.177, 0.034 |
| 25° C./60% RH | 2 week (t = 0, t = 24 hr) | 272, 194 | 0.233, 0.046 |
| | 1 month (t = 0, t = 4 hr) | 239, 193 | 0.153, 0.049 |
| 40° C./75% RH | 2 week (t = 0, t = 24 hr) | 284, 195 | 0.198, 0.083 |
| | 1 month (t = 0, t = 4 hr) | 229, 205 | 0.116, 0.056 |
| 45% SDI lot: BREC1678-054 | | | |
| Initial | Initial (t = 0, t = 24 hr) | 196, 182 | 0.070, 0.035 |
| 5° C. | 2 week (t = 0, t = 24 hr) | 223, 189 | 0.119, 0.032 |
| | 1 month (t = 0, t = 4 hr) | 206, 182 | 0.068, 0.053 |
| 25° C./60% RH | 2 week (t = 0, t = 24 hr) | 223, 194 | 0.151, 0.042 |
| | 1 month (t = 0, t = 4 hr) | 225, 191 | 0.096, 0.054 |
| 40° C./75% RH | 2 week (t = 0, t = 24 hr) | 229, 192 | 0.130, 0.048 |
| | 1 month (t = 0, t = 4 hr) | 221, 205 | 0.111, 0.054 |

Water content is summarized in Table 5-8, and is very low for all composition samples and all conditions at 1-month. Water content for 40% API composition samples at all conditions at 1 month is slightly higher than initial, but still relatively dry. Water content has slightly increased (<0.1% water) versus 2-week data shown in Table 5-4.

TABLE 5-8

Water content of SDi samples on stability for 1 month verses initial values

| Sample | Condition | % Water |
|---|---|---|
| 40% AC-1204 SDI Lot: BREC1678-034 | Initial | 0.47 ± 0.01 |
| | 1 mo @ 5° C. | 0.77 ± 0.02 |
| | 1 mo @ 25° C./60% RH | 0.76 ± 0.00 |
| | 1 mo @ 40° C./75% RH | 0.74 ± 0.00 |
| 45% AC-1204 SDI Lot: BREC1678-054 | Initial | 0.58 ± 0.01 |
| | 1 mo @ 5° C. | 0.68 ± 0.01 |
| | 1 mo @ 25° C./60% RH | 0.68 ± 0.01 |
| | 1 mo @ 40° C./75% RH | 0.64 ± 0.01 |

DSC thermal events show for all conditions that the 40% and 45% API compositions after 1 month storage are similar (data not shown). The congealing temperature upon cooling is approximately −31° C. for both compositions at all conditions, but enthalpy is slightly higher for the 45% API composition compared to the 40% API composition. Exotherm 2 and Melt temperature upon heating is very similar for all samples, and again—the enthalpies are slightly larger for the 45% API composition compared to the 40% API composition. There is no significant difference verses the 2 week data.

Assay and purity measured for the 40% API composition stored 1 month is summarized and compared to initial in Table 5-9, and for the 45% API composition stored 1 month is summarized and compared to initial in Table 5-10. Assay for both compositions stored 1-month and at all conditions is near theoretical with the highest assay value at 105.7% LC and the lowest at 99.1% LC. Impurities appear to be trending to higher levels with time on stability, however, the 5° C. control sample trends at about the same magnitude suggesting that the differences potentially could be due to differences in response of the purity method.

TABLE 5-9

Assay and Purity for the 40% API composition stored 1-month

| RRT | Peak ID | 40% SDi, Initial | 40% SDi, 5 C., 2 wk | 40% SDi, 5 C., 1 mo | 40% SDi, 25 C./ 60% RH, 2 wk | 40% SDi, 25 C./ 60% RH, 1 mo | 40% SDi, 40 C./ 75% RH, 2 wk | 40% SDi, 40 C./ 75% RH, 1 mo |
|---|---|---|---|---|---|---|---|---|
| 0.21 | | ND | ND | ND | ND | ND | ND | 0.10% |
| 0.31* | | 0.15% | 0.19% | 0.26% | 0.20% | 0.27% | 0.20% | 0.28% |
| 0.34* | | 0.07% | 0.11% | 0.14% | 0.12% | 0.14% | 0.11% | 0.16% |
| 0.81 | C6:C8:C8 | 0.16% | 0.20% | 0.20% | 0.20% | 0.21% | 0.20% | 0.22% |
| 0.91 | | 0.07% | 0.12% | 0.11% | 0.12% | 0.11% | 0.12% | 0.11% |
| 1.00 | Caprylic Triglyceride | 96.04% | 95.57% | 95.35% | 95.51% | 95.31% | 95.37% | 95.09% |
| 1.04 | | ND | ND | ND | ND | 0.08% | ND | ND |
| 1.05 | | ND | ND | ND | ND | 0.07% | ND | 0.06% |
| 1.10 | | 0.26% | 0.29% | 0.27% | 0.29% | 0.29% | 0.31% | 0.30% |
| 1.19 | C10:C8:C8 | 2.14% | 2.21% | 2.28% | 2.30% | 2.32% | 2.29% | 2.34% |
| 1.29 | | ND | ND | 0.06% | ND | 0.06% | ND | 0.06% |
| 1.30 | | ND | 0.07% | 0.07% | 0.07% | 0.08% | 0.07% | 0.08% |
| 1.32 | | 0.05% | 0.09% | ND | 0.08% | ND | 0.09% | ND |
| 1.35 | | 0.90% | 0.97% | 0.97% | 1.02% | 0.98% | 1.03% | 1.00% |
| 1.42 | | ND | ND | 0.09% | ND | 0.07% | ND | 0.08% |
| 1.48 | | 0.18% | 0.23% | 0.20% | 0.23% | 0.19% | 0.24% | 0.18% |
| 1.61 | | <LOQ | ND | ND | ND | ND | ND | ND |
| — | Total Impurities | 3.96% | 4.43% | 4.65% | 4.49% | 4.79% | 4.63% | 4.91% |
| — | Assay | 100.8% ± 0.1% | 103.8% ± 1.8% | 101.1% ± 1.0% | 105.7% ± 0.1% | 101.8% ± 1.6% | 101.2% ± 5.3% | 100.6% ± 0.6% |

ND = not detected,
LOQ > 0.05%
*RRT 0.31 & 0.34 were corrected for contribution from Capmul 808G

TABLE 5-10

Assay and Purity for the 45% API composition stored 1-month

| RRT | Peak ID | 45% SDi, Initial | 45% SDi, 5 C., 2 wk | 45% SDi, 5 C., 1 mo | 45% SDi, 25 C./ 60% RH, 2 wk | 45% SDi, 25 C./ 60% RH, 1 mo | 45% SDi, 40 C./ 75% RH, 2 wk | 45% SDi, 40 C./ 75% RH, 1 mo |
|---|---|---|---|---|---|---|---|---|
| 0.24 | | 0.06% | ND | ND | ND | ND | ND | ND |
| 0.31* | | 0.16% | 0.20% | 0.27% | 0.20% | 0.31% | 0.22% | 0.34% |
| 0.34* | | 0.08% | 0.11% | 0.15% | 0.11% | 0.17% | 0.12% | 0.19% |
| 0.81 | C6:C8:C8 | 0.16% | 0.20% | 0.21% | 0.21% | 0.21% | 0.21% | 0.21% |
| 0.91 | | 0.08% | 0.11% | 0.10% | 0.12% | 0.11% | 0.12% | 0.11% |
| 1.00 | Caprylic Triglyceride | 95.98% | 95.48% | 95.34% | 95.36% | 95.15% | 95.29% | 95.07% |
| 1.08 | | ND | ND | ND | ND | 0.17% | ND | 0.07% |
| 1.10 | | 0.25% | 0.30% | 0.28% | 0.30% | 0.30% | 0.30% | 0.30% |
| 1.19 | C10:C8:C8 | 2.15% | 2.28% | 2.27% | 2.30% | 2.33% | 2.32% | 2.33% |
| 1.29 | | ND | ND | ND | ND | ND | ND | ND |
| 1.30 | | <LOQ | 0.08% | 0.06% | 0.07% | 0.06% | 0.07% | 0.06% |
| 1.32 | | 0.05% | ND | 0.08% | 0.08% | 0.08% | 0.08% | 0.08% |
| 1.35 | | 0.91% | 1.00% | 0.98% | 1.01% | 1.00% | 1.03% | 1.00% |
| 1.42 | | ND | ND | 0.07% | ND | 0.08% | ND | 0.08% |

TABLE 5-10-continued

Assay and Purity for the 45% API composition stored 1-month

| RRT | Peak ID | 45% SDi, Initial | 45% SDi, 5 C., 2 wk | 45% SDi, 5 C., 1 mo | 45% SDi, 25 C./ 60% RH, 2 wk | 45% SDi, 25 C./ 60% RH, 1 mo | 45% SDi, 40 C./ 75% RH, 2 wk | 45% SDi, 40 C./ 75% RH, 1 mo |
|---|---|---|---|---|---|---|---|---|
| 1.48 | | 0.18% | 0.24% | 0.18% | 0.23% | 0.18% | 0.24% | 0.20% |
| 1.61 | | ND | ND | ND | ND | ND | ND | ND |
| — | Total Impurities | 4.02% | 4.52% | 4.66% | 4.64% | 4.85% | 4.71% | 4.93% |
| — | Assay | 101.1% ± 1% | 102.1% ± 2.9% | 100.8% ± 2.0% | 102.4% ± 1.2% | 100.5% ± 1.2% | 105.5% ± 1.1% | 99.1% ± 2.3% |

ND = not detected,
LOQ > 0.05%
*RRT 0.31 & 0.34 were corrected for contribution from Capmul 808G All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A spray dried pharmaceutical powder composition comprising: an active agent consisting of caprylic triglyceride having a purity of at least 95%; at least one surfactant selected from the group consisting of polyoxyl hydrogenated castor oil, polyoxyl stearate, polyoxyl hydroxystearate, lecithin, phosphatidylcholine, and combinations thereof; an adsorbent; and a film forming polymer selected from polyvinylpyrrolidone (PVP) or polyvinylpyrrolidone-vinyl acetate copolymer (PVP-VA),
   wherein the active agent is present in an amount of about 40% to about 65% by weight of the total composition; and
   wherein the composition is a self-emulsifying, spray dried powder composition comprising spray dried particles having an average diameter of between about 5 µm and about 50 µm.

2. The spray dried pharmaceutical powder composition of claim 1, wherein the spray dried pharmaceutical composition forms an emulsion in an aqueous use environment that is stable for at least about 4 hours at ambient conditions.

3. The spray dried pharmaceutical powder composition of claim 2, wherein the emulsion forms droplets having an average droplet size of between about 200 nm and 300 nm.

4. The spray dried pharmaceutical powder composition of claim 1, wherein the composition comprises at least two surfactants.

5. The spray dried solid pharmaceutical powder composition of claim 4, wherein at least one of the at least two surfactants includes a polyoxyl hydrogenated castor oil.

6. The spray dried pharmaceutical powder composition of claim 5, wherein the polyoxyl hydrogenated castor oil is present in an amount of at least 2.5% by weight of the total composition.

7. The spray dried pharmaceutical powder composition of claim 4, wherein the ratio of the at least two surfactants is about 1:1 by weight, relative to one another.

8. The spray dried pharmaceutical powder composition of claim 1, further comprising a co-surfactant.

9. The spray dried pharmaceutical powder composition of claim 8, wherein the co-surfactant is selected from glyceryl caprylate, glyceryl monocaprylate, lauroglycol, and combinations thereof.

10. The spray dried pharmaceutical powder composition of claim 1, wherein the adsorbent is a fumed silica.

11. The spray dried pharmaceutical powder composition of claim 10, wherein the fumed silica is present in an amount of at least about 2 wt % of the total composition.

12. The spray dried pharmaceutical powder composition of claim 1, wherein the film forming polymer is present in an amount of at least about 8 wt % of the total composition.

13. A method of treating a disease or disorder associated with reduced cognitive function in a subject in need thereof, the method comprising administering to the subject the spray dried pharmaceutical powder compositoin of claim 1 in an amount effective to elevate ketone body concentrations in said subject to thereby treat said disease or disorder.

14. The method of claim 13, wherein the disease or disorder associated with reduced cognitive function is selected from Alzheimer's disease and Age-Associated Memory Impairment.

15. The method of claim 13, further comprising determining if the patient lacks the ApoE4 genotype.

16. The method of claim 13, wherein the composition is administered at a dose of about 0.05 g/kg/day to about 10 g/kg/day.

17. A pharmaceutical composition comprising: an active agent consisting of caprylic triglyceride having a purity of at least 95% and at least two surfactants independently selected from the group consisting of polyoxyl hydrogenated castor oil, polyoxyl stearate, polyoxyl hydroxystearate, lecithin, phosphatidylcholine, and combinations thereof,
   wherein the caprylic triglyceride is present in an amount of about 40% to about 65% by weight of the total composition,
   and wherein the pharmaceutical composition forms a stable emulsion for at least about 4 hours at ambient conditions and wherein the emulsion forms droplets having an average droplet size of between 200 nm and 300 nm.

18. The pharmaceutical composition of claim 17, wherein each of the at least two surfactants are independently present in an amount of at least 2.0% by weight of the total composition.

19. The pharmaceutical composition of claim 17, wherein the at least two surfactants are present at a 1:1 to 2:1 ratio, relative to one another.

20. The pharmaceutical composition of claim 17, further comprising a co-surfactant.

21. The pharmaceutical composition of claim 20, wherein the co-surfactant is selected from glyceryl caprylate, glyceryl monocaprylate, lauroglycol, and combinations thereof.

22. A method of treating a disease or disorder associated with reduced cognitive function in a subject in need thereof, the method comprising administering to the subject the pharmaceutical composition of claim 17 in an amount effective to elevate ketone body concentrations in said subject to thereby treat said disease or disorder.

23. The method of claim 22, wherein the disease or disorder associated with reduced cognitive function is selected from Alzheimer's disease and Age-Associated Memory Impairment.

24. The method of claim 22, further comprising determining if the patient lacks the ApoE4 genotype.

25. The method of claim 22, wherein the composition is administered at a dose of about 0.05 g/kg/day to about 10 g/kg/day.

* * * * *

UNITED STATES PATENT AND TRADEMARK OFFICE
CERTIFICATE OF CORRECTION

| | |
|---|---|
| PATENT NO. | : 11,559,488 B2 |
| APPLICATION NO. | : 16/493963 |
| DATED | : January 24, 2023 |
| INVENTOR(S) | : Aaron M. Badenoch et al. |

It is certified that error appears in the above-identified patent and that said Letters Patent is hereby corrected as shown below:

In the Claims (Claim 5) Column 35, Line 65, delete "solid".

(Claim 13) Column 36, Line 4, replace "compositoin" with "composition".

Signed and Sealed this
Thirtieth Day of May, 2023

Katherine Kelly Vidal
*Director of the United States Patent and Trademark Office*